United States Patent
Messerly et al.

(10) Patent No.: US 10,772,656 B2
(45) Date of Patent: Sep. 15, 2020

(54) ULTRASONIC SURGICAL SHEARS WITH CLAMPING FEATURE

(71) Applicant: Ethicon LLC, Guaynabo, PR (US)

(72) Inventors: Jeffrey D. Messerly, Cincinnati, OH (US); David A. Witt, Maineville, OH (US); Foster B. Stulen, Mason, OH (US); Christopher A. Papa, Cincinnati, OH (US); Vincent P. Battaglia, Jr., Lebanon, OH (US)

(73) Assignee: Ethicon LLC, Guaynabo, PR (US)

( * ) Notice: Subject to any disclaimer, the term of this patent is extended or adjusted under 35 U.S.C. 154(b) by 242 days.

(21) Appl. No.: 15/860,896

(22) Filed: Jan. 3, 2018

(65) Prior Publication Data
US 2018/0153575 A1 Jun. 7, 2018

Related U.S. Application Data

(63) Continuation of application No. 13/834,248, filed on Mar. 15, 2013, now Pat. No. 9,895,161.

(51) Int. Cl.
*A61B 17/32* (2006.01)

(52) U.S. Cl.
CPC .......... *A61B 17/320092* (2013.01); *A61B 2017/320093* (2017.08); *A61B 2017/320094* (2017.08); *A61B 2017/320095* (2017.08); *A61B 2017/320097* (2017.08)

(58) Field of Classification Search
CPC ............................................. A61B 17/320092; A61B 2017/320094; A61B 2017/320095; A61B 2017/320097; A61B 2017/320093
See application file for complete search history.

(56) References Cited

U.S. PATENT DOCUMENTS

| | | | |
|---|---|---|---|
| 5,322,055 A | 6/1994 | Davison et al. |
| 5,873,873 A | 2/1999 | Smith et al. |
| 5,980,510 A | 11/1999 | Tsonton et al. |

(Continued)

FOREIGN PATENT DOCUMENTS

| | | | |
|---|---|---|---|
| JP | 3270415 B2 | 4/2002 |
| JP | 2002-306503 A | 10/2002 |

(Continued)

OTHER PUBLICATIONS

Chinese Office Action, Notification of the First Office Action, dated Apr. 6, 2017 for Application No. 201480015361.1, 11 pgs.

(Continued)

*Primary Examiner* — Ashley L Fishback
(74) *Attorney, Agent, or Firm* — Frost Brown Todd LLC

(57) ABSTRACT

An apparatus for operating on tissue comprises a shaft, an acoustic waveguide, and an end effector. The acoustic waveguide extends along the shaft and is configured to transmit ultrasonic vibration. The end effector comprises an ultrasonic blade and a clamp arm. The ultrasonic blade is in acoustic communication with the acoustic waveguide. The clamp arm is pivotable toward the ultrasonic blade. The end effector defines a first longitudinal region and a second longitudinal region. The end effector is configured to clamp tissue between the clamp arm and the ultrasonic blade in the first longitudinal region. The end effector is configured to sever tissue with the ultrasonic blade in the second longitudinal region.

20 Claims, 18 Drawing Sheets

(56) References Cited

U.S. PATENT DOCUMENTS

| | | | |
|---|---|---|---|
| 6,214,023 | B1 | 4/2001 | Whipple et al. |
| 6,325,811 | B1 | 12/2001 | Messerly |
| 6,340,352 | B1 | 1/2002 | Okada et al. |
| 6,569,178 | B1 | 5/2003 | Miyawaki et al. |
| 6,669,690 | B1 | 12/2003 | Okada et al. |
| 6,783,524 | B2 | 8/2004 | Anderson et al. |
| 7,645,278 | B2 | 1/2010 | Ichihashi et al. |
| 8,142,461 | B2 | 3/2012 | Houser et al. |
| 8,328,834 | B2 | 12/2012 | Isaacs et al. |
| 8,461,744 | B2 | 6/2013 | Wiener et al. |
| 8,523,889 | B2 | 9/2013 | Stulen et al. |
| 8,591,536 | B2 | 11/2013 | Robertson |
| 8,986,302 | B2 | 3/2015 | Aldridge et al. |
| 9,023,071 | B2 | 5/2015 | Miller et al. |
| 9,095,367 | B2 | 8/2015 | Olson et al. |
| 9,259,265 | B2 | 2/2016 | Houser et al. |
| 9,381,058 | B2 | 7/2016 | Houser et al. |
| 9,393,037 | B2 | 7/2016 | Olson et al. |
| 9,402,682 | B2 | 8/2016 | Worrell et al. |
| 9,895,161 | B2 | 2/2018 | Messerly et al. |
| 2006/0079874 | A1 | 4/2006 | Faller et al. |
| 2007/0191713 | A1 | 8/2007 | Eichmann et al. |
| 2007/0282333 | A1 | 12/2007 | Fortson et al. |
| 2008/0200940 | A1 | 8/2008 | Eichmann et al. |
| 2009/0143806 | A1 | 6/2009 | Witt et al. |
| 2010/0063527 | A1* | 3/2010 | Beaupre ......... A61B 17/320092 606/169 |
| 2012/0116265 | A1 | 5/2012 | Houser et al. |

FOREIGN PATENT DOCUMENTS

| | | |
|---|---|---|
| JP | 4402629 B2 | 11/2009 |
| JP | 5575490 B2 | 8/2014 |

OTHER PUBLICATIONS

International Search Report dated Oct. 27, 2014 for Application No. PCT/US2014/022462.

International Preliminary Report on Patentability dated Feb. 15, 2015 for Application No. PCT/US2014/022462.

Japanese Office Action, Notifications of Reasons for Refusal, dated Jan. 23, 2018 for Application No. JP 2016-500975, 11 pgs.

Japanese Search Report, Search Report by Registered Searching Organization, dated Jan. 19, 2018 for Application No. JP 2016-500975, 21 pgs.

U.S. Appl. No. 61/410,603, filed Nov. 5, 2010.

* cited by examiner

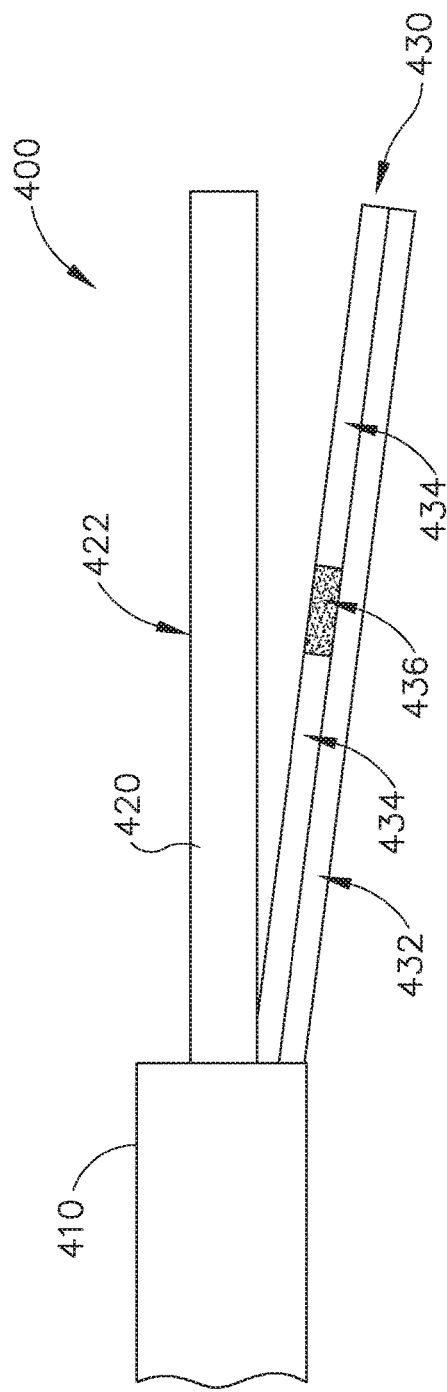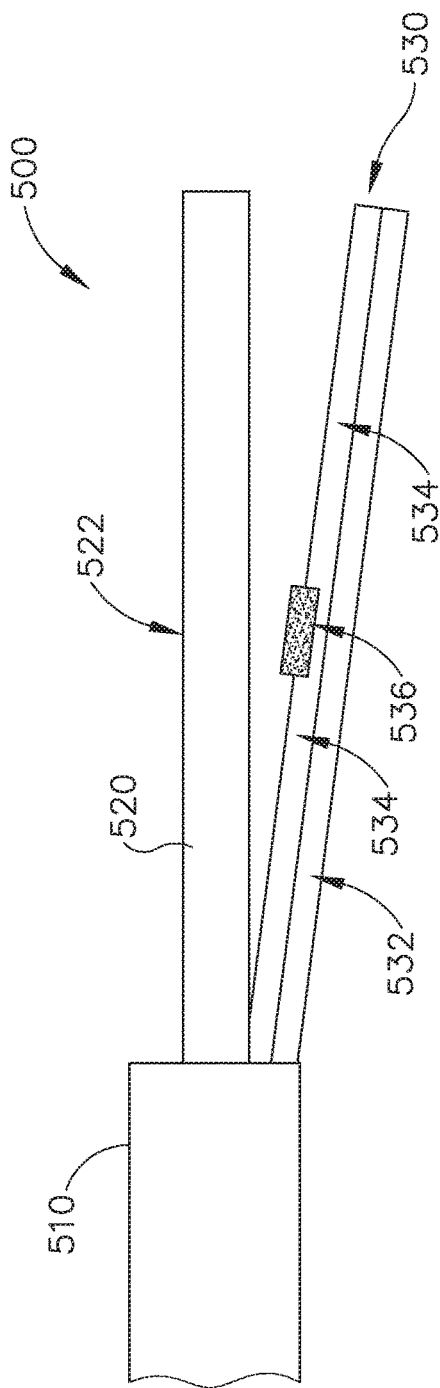

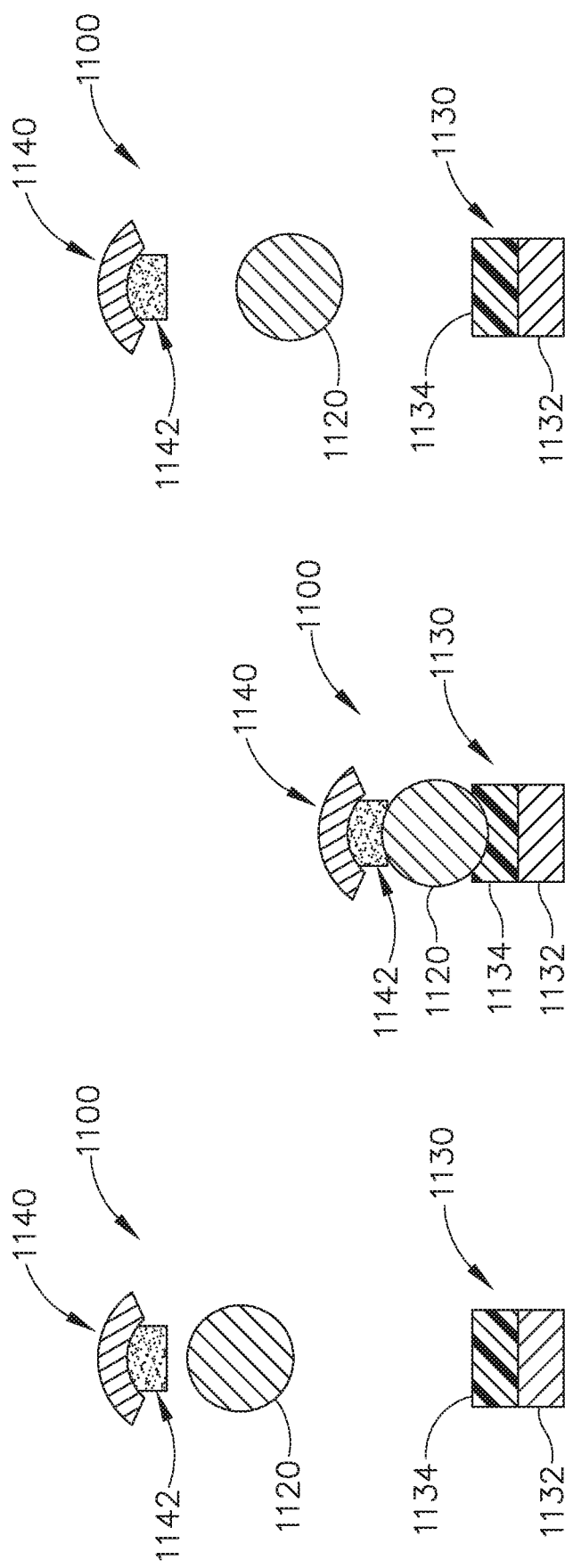

ULTRASONIC SURGICAL SHEARS WITH CLAMPING FEATURE

This application is a continuation of U.S. application Ser. No. 13/834,248, filed Mar. 15, 2013, published as U.S. Pub. No. 2014/0277029 on Sep. 18, 2014, issued as U.S. Pat. No. 9,895,161, on Feb. 20, 2018, entitled "Ultrasonic Surgical Shears with Clamping Feature."

BACKGROUND

A variety of surgical instruments include an end effector having a blade element that vibrates at ultrasonic frequencies to cut and/or seal tissue (e.g., by denaturing proteins in tissue cells). These instruments include piezoelectric elements that convert electrical power into ultrasonic vibrations, which are communicated along an acoustic waveguide to the blade element. Examples of such ultrasonic surgical instruments include the HARMONIC ACE® Ultrasonic Shears, the HARMONIC WAVE® Ultrasonic Shears, the HARMONIC FOCUS® Ultrasonic Shears, and the HARMONIC SYNERGY® Ultrasonic Blades, all by Ethicon Endo-Surgery, Inc. of Cincinnati, Ohio. Further examples of such devices and related concepts are disclosed in U.S. Pat. No. 5,322,055, entitled "Clamp Coagulator/Cutting System for Ultrasonic Surgical Instruments," issued Jun. 21, 1994, the disclosure of which is incorporated by reference herein; U.S. Pat. No. 5,873,873, entitled "Ultrasonic Clamp Coagulator Apparatus Having Improved Clamp Mechanism," issued Feb. 23, 1999, the disclosure of which is incorporated by reference herein; U.S. Pat. No. 5,980,510, entitled "Ultrasonic Clamp Coagulator Apparatus Having Improved Clamp Arm Pivot Mount," filed Oct. 10, 1997, the disclosure of which is incorporated by reference herein; U.S. Pat. No. 6,325,811, entitled "Blades with Functional Balance Asymmetries for use with Ultrasonic Surgical Instruments," issued Dec. 4, 2001, the disclosure of which is incorporated by reference herein; U.S. Pat. No. 6,783,524, entitled "Robotic Surgical Tool with Ultrasound Cauterizing and Cutting Instrument," issued Aug. 31, 2004, the disclosure of which is incorporated by reference herein; U.S. Pub. No. 2006/0079874, entitled "Tissue Pad for Use with an Ultrasonic Surgical Instrument," published Apr. 13, 2006, now abandoned, the disclosure of which is incorporated by reference herein; U.S. Pub. No. 2007/0191713, entitled "Ultrasonic Device for Cutting and Coagulating," published Aug. 16, 2007, now abandoned, the disclosure of which is incorporated by reference herein; U.S. Pub. No. 2007/0282333, entitled "Ultrasonic Waveguide and Blade," published Dec. 6, 2007, now abandoned, the disclosure of which is incorporated by reference herein; U.S. Pub. No. 2008/0200940, entitled "Ultrasonic Device for Cutting and Coagulating," published Aug. 21, 2008, now abandoned, the disclosure of which is incorporated by reference herein; U.S. Pub. No. 2010/0069940, entitled "Ultrasonic Device for Fingertip Control," published Mar. 18, 2010, now U.S. Pat. No. 9,023,071, issued on May 5, 2015, the disclosure of which is incorporated by reference herein; and U.S. Pub. No. 2011/0015660, entitled "Rotating Transducer Mount for Ultrasonic Surgical instruments," published Jan. 20, 2011, now U.S. Pat. No. 8,461,744, issued on Jun. 11, 2013, the disclosure of which is incorporated by reference herein; U.S. Pub. No. 2012/0029546, entitled "Ultrasonic Surgical Instrument Blades," published Feb. 2, 2012, now U.S. Pat. No. 8,591,536, issued on Nov. 26, 2013, the disclosure of which is incorporated by reference herein; U.S. patent application Ser. No. 13/538,588, filed Jun. 29, 2012, entitled "Surgical Instruments with Articulating Shafts," now U.S. Pat. No. 9,393,037, issued on Jul. 19, 2016, the disclosure of which is incorporated by reference herein; and U.S. patent application Ser. No. 13/657,553, filed Oct. 22, 2012, entitled "Flexible Harmonic Waveguides/Blades for Surgical instruments," now U.S. Pat. No. 9,095,367, issued on Aug. 4, 2015, the disclosure of which is incorporated by reference herein.

Additionally, some of the foregoing surgical tools may include a cordless transducer such as that disclosed in U.S. Pub. No. 2012/0112687, entitled "Recharge System for Medical Devices," published May 10, 2012, now U.S. Pat. No. 9,381,058, issued on Jul. 5, 2016, the disclosure of which is incorporated by reference herein; U.S. Pub. No. 2012/0116265, now abandoned, entitled "Surgical Instrument with Charging Devices," published May 10, 2012, the disclosure of which is incorporated by reference herein; and/or U.S. Pat. App. No. 61/410,603, filed Nov. 5, 2010, entitled "Energy-Based Surgical Instruments," the disclosure of which is incorporated by reference herein.

While several surgical instruments and systems have been made and used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 13 depicts a partial side elevational view of another exemplary alternative end effector suitable for incorporation in the instrument of FIG. 1;

FIG. 14 depicts a partial side elevational view of another exemplary alternative end effector suitable for incorporation in the instrument of FIG. 1;

FIG. 30 depicts a sectional view of the end effector of FIG. 27, with the features positioned as shown in FIG. 27;

FIG. 31 depicts a sectional of the end effector of FIG. 27, with the features positioned as shown in FIG. 28; and FIG. 32 depicts a sectional view of the end effector of FIG. 27, with the features positioned as shown in FIG. 29.

Figure 1:
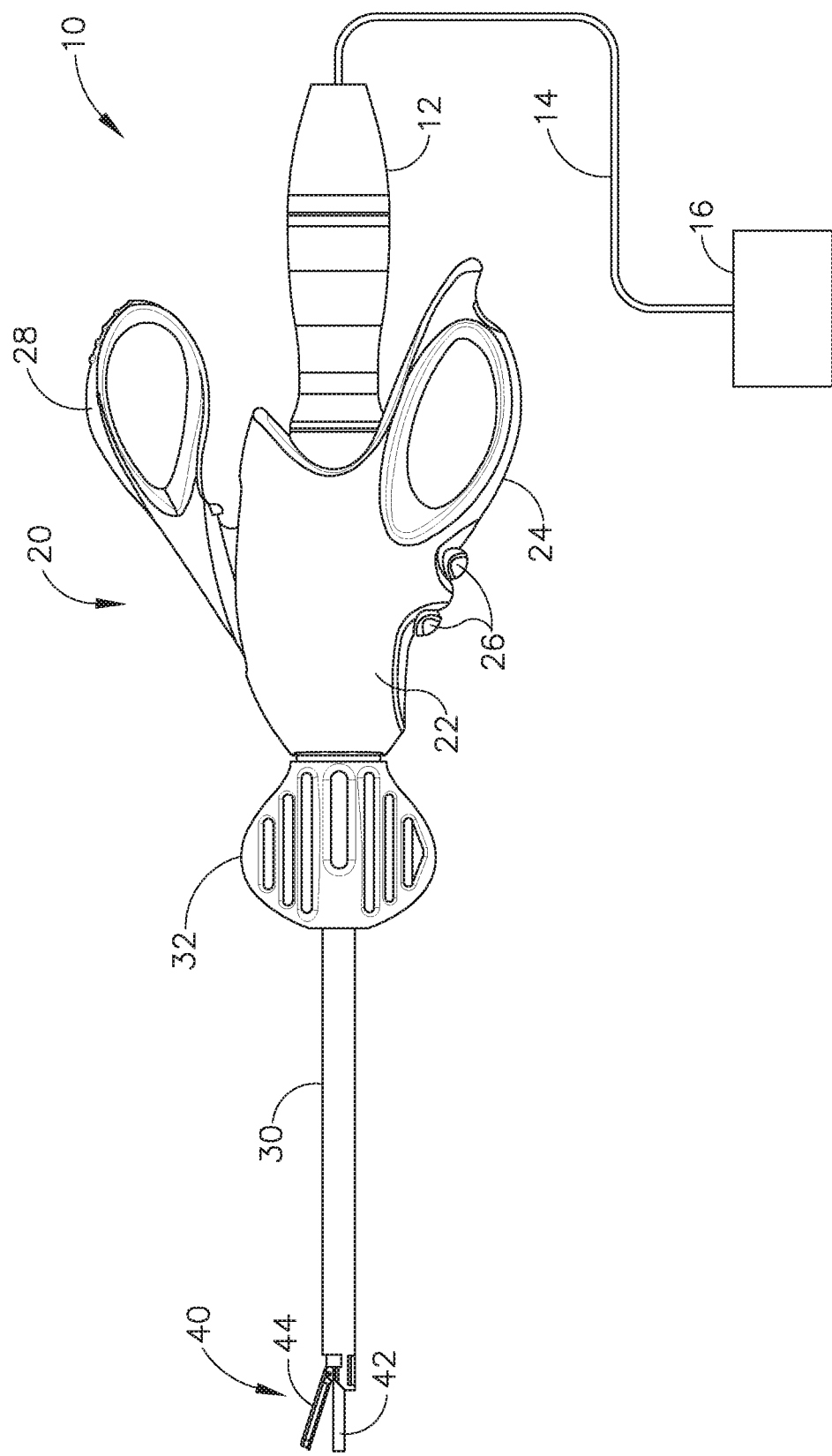
FIG. 1 depicts a side elevational view of an exemplary ultrasonic surgical instrument.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to a robotic surgical driver comprising a proximal housing having an interface that mechanically and electrically couples with a surgical instrument having a distal surgical end effector. The term "proximal" refers the position of an element closer to the robotic surgical driver housing and the term "distal" refers to the position of an element closer to the surgical end effector of the surgical instrument and further away from the housing.

I. Exemplary Ultrasonic Surgical Instrument

FIG. 1 illustrates an exemplary ultrasonic surgical instrument (10). At least part of instrument (10) may be constructed and operable in accordance with at least some of the teachings of U.S. Pat. Nos. 5,322,055; 5,873,873; 5,980,510; 6,325,811; 6,783,524; U.S. Pub. Nos. 2006/0079874, now abandoned; 2007/0191713, now abandoned; 2007/0282333, now abandoned; 2008/0200940, now abandoned; 2010/0069940, now U.S. Pat. No. 9,023,071; U.S. Pub. No. 2011/0015660, now U.S. Pat. No. 8,461,744; U.S. Pub. No. 2012/0112687, now U.S. Pat. No. 9,381,058; U.S. Pub. No. 2012/0116265, now abandoned; U.S. patent application Ser. No. 13/538,588, now U.S. Pat. No. 9,393,037; U.S. patent application Ser. No. 13/657,553, now U.S. Pat. No. 9,095,367; and/or U.S. Pat. App. No. 61/410,603. The disclosures of each of the foregoing patents, publications, and applications are incorporated by reference herein. As described therein and as will be described in greater detail below, instrument (10) is operable to cut tissue and seal or weld tissue (e.g., a blood vessel, etc.) substantially simultaneously. In other words, instrument (10) operates similar to an endocutter type of stapler, except that instrument (10) provides tissue welding through application of ultrasonic vibrational energy instead of providing lines of staples to join tissue. This same ultrasonic vibrational energy also separates tissue similar to severing of tissue by a translating knife member. It should also be understood that instrument (10) may have various structural and functional similarities with the HARMONIC ACE® Ultrasonic Shears, the HAR- MONIC WAVE® Ultrasonic Shears, the HARMONIC FOCUS® Ultrasonic Shears, and/or the HARMONIC SYNERGY® Ultrasonic Blades. Furthermore, instrument (10) may have various structural and functional similarities with the devices taught in any of the other references that are cited and incorporated by reference herein.

To the extent that there is some degree of overlap between the teachings of the references cited herein, the HARMONIC ACE® Ultrasonic Shears, the HARMONIC WAVE® Ultrasonic Shears, the HARMONIC FOCUS® Ultrasonic Shears, and/or the HARMONIC SYNERGY® Ultrasonic Blades, and the following teachings relating to instrument (10), there is no intent for any of the description herein to be presumed as admitted prior art. Several teachings herein will in fact go beyond the scope of the teachings of the references cited herein and the HARMONIC ACE® Ultrasonic Shears, the HARMONIC WAVE® Ultrasonic Shears, the HARMONIC FOCUS® Ultrasonic Shears, and the HARMONIC SYNERGY® Ultrasonic Blades.

Instrument (10) of the present example comprises a handpiece (20), a shaft assembly (30), and an end effector (40). Handpiece (20) comprises a body (22) including a finger grip (24) and a pair of buttons (26). Handpiece (20) also includes a trigger (28) that is pivotable toward and away from body (22). Trigger (28) and finger grip (24) together provide a scissor grip type of configuration. It should be understood, however, that various other suitable configurations may be used, including but not limited to a pistol grip configuration. End effector (40) includes an ultrasonic blade (42) and a pivoting clamp arm (44). Clamp arm (44) is coupled with trigger (28) such that clamp arm (44) is pivotable toward ultrasonic blade (42) in response to pivoting of trigger (28) toward body (22); and such that clamp arm (44) is pivotable away from ultrasonic blade (42) in response to pivoting of trigger (28) away from body (22). Various suitable ways in which clamp arm (44) may be coupled with trigger (28) will be apparent to those of ordinary skill in the art in view of the teachings herein. In some versions, one or more resilient members are used to bias clamp arm (44) and/or trigger (28) to the open position shown in FIG. 1.

An ultrasonic transducer assembly (12) extends proximally from body (22) of handpiece (20). Transducer assembly (12) is coupled with a generator (16) via a cable (14). Transducer assembly (12) receives electrical power from generator (16) and converts that power into ultrasonic vibrations through piezoelectric principles. Generator (16) may include a power source and control module that is configured to provide a power profile to transducer assembly (12) that is particularly suited for the generation of ultrasonic vibrations through transducer assembly (12). By way of example only, generator (16) may comprise a GEN 300 sold by Ethicon Endo-Surgery, Inc. of Cincinnati, Ohio. In addition or in the alternative, generator (16) may be constructed in accordance with at least some of the teachings of U.S. Pub. No. 2011/0087212, entitled "Surgical Generator for Ultrasonic and Electrosurgical Devices," published Apr. 14, 2011, now U.S. Pat. No. 8,986,302, issued on Mar. 24, 2015, the disclosure of which is incorporated by reference herein. It should also be understood that at least some of the functionality of generator (16) may be integrated into handpiece (20), and that handpiece (20) may even include a battery or other on-board power source such that cable (14) is omitted. Still other suitable forms that generator (16) may take, as well as various features and operabilities that generator (300) may provide, will be apparent to those of ordinary skill in the art in view of the teachings herein.

Ultrasonic vibrations that are generated by transducer assembly (12) are communicated along an acoustic waveguide (not shown), which extends through shaft assembly (30) to reach ultrasonic blade (42). Blade (42) is thus operable to effectively cut through and seal tissue, particularly when the tissue is being clamped between clamp arm (44) and blade (42). It should be understood that the waveguide may be configured to amplify mechanical vibrations transmitted through the waveguide. Furthermore, either the waveguide may include features operable to control the gain of the longitudinal vibrations along the waveguide and/or features to tune the waveguide to the resonant frequency of the system. Buttons (26) are operable to selectively activate transducer assembly (12), to thereby activate ultrasonic blade (42). In the present example, two buttons (26) are provided—one for activating ultrasonic blade (42) at a low power and another for activating ultrasonic blade (42) at a high power. However, it should be understood that any other suitable number of buttons and/or otherwise selectable power levels may be provided.

In the present example, the distal end of ultrasonic blade (42) is located at a position corresponding to an anti-node associated with resonant ultrasonic vibrations communicated through the waveguide, in order to tune the acoustic assembly to a preferred resonant frequency $f_o$ when the acoustic assembly is not loaded by tissue. When transducer assembly (12) is energized, the distal end of ultrasonic blade (42) is configured to move longitudinally in the range of, for example, approximately 10 to 500 microns peak-to-peak, and in some instances in the range of about 20 to about 200 microns at a predetermined vibratory frequency $f_o$ of, for example, 55.5 kHz. When transducer assembly (12) of the present example is activated, these mechanical oscillations are transmitted through the waveguide to reach ultrasonic blade (42), thereby providing oscillation of ultrasonic blade (42) at the resonant ultrasonic frequency. Thus, when tissue is secured between ultrasonic blade (42) and clamp arm (44), the ultrasonic oscillation of ultrasonic blade (42) may simultaneously sever the tissue and denature the proteins in adjacent tissue cells, thereby providing a coagulative effect with relatively little thermal spread. In some versions, an electrical current may also be provided through ultrasonic blade (42) and clamp arm (44) to also cauterize the tissue. While some configurations for an acoustic transmission assembly and transducer assembly (12) have been described, still other suitable configurations for an acoustic transmission assembly and transducer assembly (12) will be apparent to one or ordinary skill in the art in view of the teachings herein. Similarly, other suitable configurations for end effector (40) will be apparent to those of ordinary skill in the art in view of the teachings herein.

In the present example, shaft assembly (30) is configured to selectively couple with transducer assembly (12). To assist in proper coupling, a torque wrench (32) is included about shaft assembly (30). Torque wrench (32) is configured to facilitate gripping of shaft assembly (30) as shaft assembly (30) is rotated relative to transducer assembly (12) during coupling. In addition, torque wrench (32) is configured to provide audible and/or tactile feedback once the appropriate amount of torque as been achieved to provide a coupling of transducer assembly (12) and shaft assembly (30) at the appropriate tightness. For instance, torque wrench (32) may provide a pair of audible and tactile clicks once the appropriate level of torque/tightness has been achieved. Other variations of torque wrench (32) will be apparent to those of ordinary skill in the art in view of the teachings herein. Furthermore, it should be understood that torque wrench (32) may simply be omitted, if desired.

In some versions, shaft assembly (30) includes an articulation section enabling end effector (40) to be angularly deflected laterally away from the longitudinal axis defined by shaft assembly (30). By way of example only, such an articulation section may be configured in accordance with one or more teachings of U.S. Pub. No. 2012/0078247, now U.S. Pat. No. 9,402,682, issued on Aug. 2, 2016, the disclosure of which is incorporated by reference herein. As another merely illustrative example, such an articulation section may be configured in accordance with one or more teachings of U.S. patent application Ser. No. 13/538,588, now U.S. Pat. No. 9,393,037, issued on Jul. 19, 2016, and/or U.S. patent application Ser. No. 13/657,553, now U.S. Pat. No. 9,095,367, issued on Aug. 4, 2015, the disclosures of which are incorporated by reference herein. Of course, some versions of shaft assembly (30) may simply lack articulation altogether.

The foregoing components and operabilities of instrument (10) are merely illustrative. Instrument (10) may be configured in numerous other ways as will be apparent to those of ordinary skill in the art in view of the teachings herein. By way of example only, at least part of instrument (10) may be constructed and/or operable in accordance with at least some of the teachings of any of the following, the disclosures of which are all incorporated by reference herein: U.S. Pat. Nos. 5,322,055; 5,873,873; 5,980,510; 6,325,811; 6,783,524; U.S. Pub. Nos. 2006/0079874, now abandoned; 2007/0191713, now abandoned; 2007/0282333, now abandoned; 2008/0200940, now abandoned; 2010/0069940, now U.S. Pat. No. 9,023,071, issued on May 5, 2015; U.S. Pub. No. 2011/0015660, now U.S. Pat. No. 8,461,744, issued on Jun. 11, 2013; U.S. Pub. No. 2012/0112687, now U.S. Pat. No. 9,381,058; U.S. Pub. No. 2012/0116265, now abandoned; U.S. patent application Ser. No. 13/538,588, now U.S. Pat. No. 9,393,037; and/or U.S. patent application Ser. No. 13/657,553, now U.S. Pat. No. 9,095,367. Additional variations for instrument (10) will be described in greater detail below. It should be understood that the below described variations may be readily applied to any of the instruments referred to in any of the references that are cited herein, among others.

II. Exemplary Alternative Ultrasonic End Effector with Dual Modes

In some instances, the operation of an ultrasonic surgical instrument provides tradeoffs between tissue cutting speed and tissue sealing effectiveness. For instance, the region of an ultrasonic blade closest to an anti-node associated with resonant ultrasonic vibrations communicated through the blade may provide the fastest tissue cutting speed; yet may be less effective at sealing tissue (e.g., particularly thick tissue). The region of an ultrasonic blade closest to a node associated with resonant ultrasonic vibrations communicated through the blade may provide the most effective tissue sealing (e.g., particularly thick tissue) by providing a uniform pressure profile and a uniform displacement profile; yet may provide a relatively slow tissue cutting speed. It may therefore be desirable to facilitate easy selection between these capabilities through a single variation of instrument (10). This may be done by establishing clearly demarcated regions in an end effector to enable the operator to readily recognize and select from the appropriate blade regions based on the particular surgical task and context at hand. Merely illustrative examples of such end effectors are shown in FIGS. 2-12 and are described in greater detail below; while other variations will be apparent to those of ordinary skill in the art in view of the teachings herein.

In the examples described below, an end effector provides a first region that is more effective for sealing tissue (e.g., through clamping between a clamp pad and an ultrasonic blade); and a second region that is more effective for cutting tissue (e.g., through a shearing action between a clamp arm and the ultrasonic blade). It should be understood, however, that the first region may still effectively cut tissue and the second region may still effectively seal tissue. In these examples, the separate regions are provided through different clamp arm configurations, while the configuration of the ultrasonic blade does not change between the separate regions. In some other versions, however, the configuration of the ultrasonic blade may in fact change between the separate regions. In either case, the ultrasonic blade may be viewed as having a working/active length that extends along both regions. In other words, the working/active length of the ultrasonic blade may be defined as the length of the first region plus the length of the second region. In some versions, the working length is approximately 4 cm. Alternatively, any other suitable working/active length may be provided.

Figure 2:
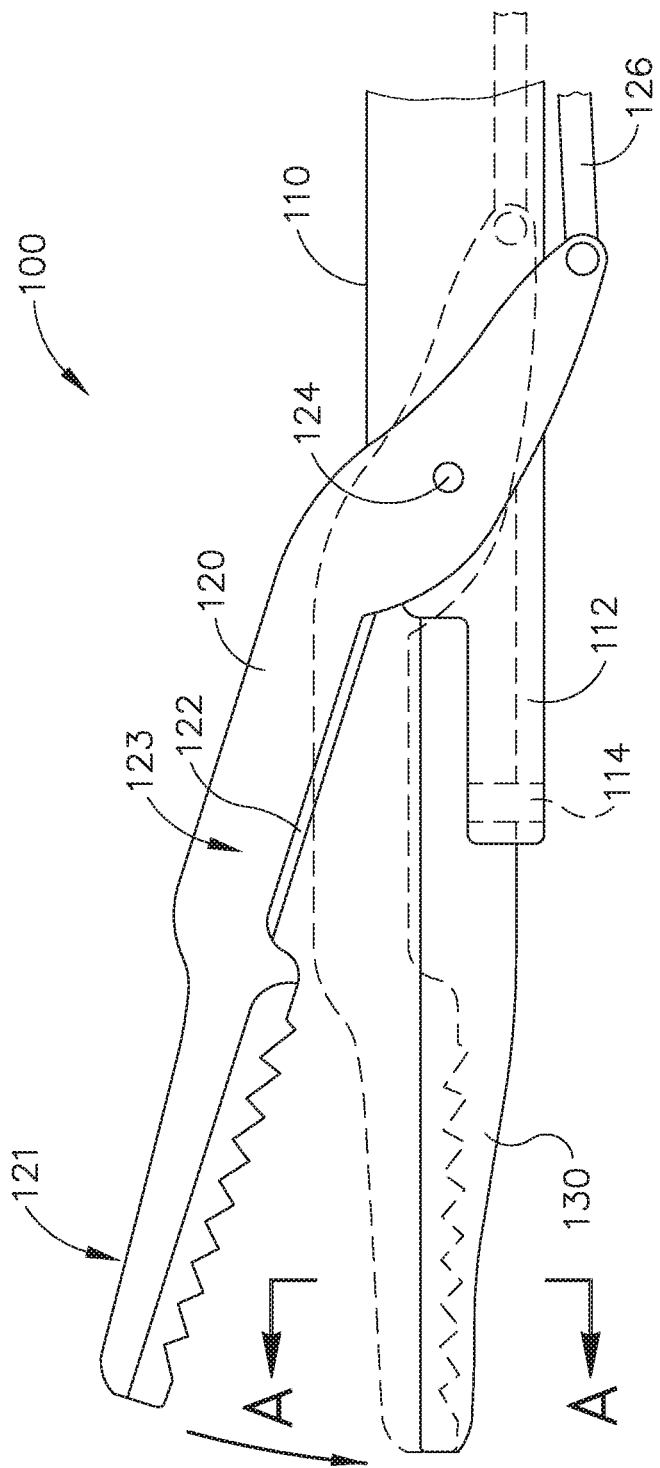
FIG. 2 depicts a partial side elevational view of an exemplary alternative end effector suitable for incorporation in the instrument of FIG. 1.

FIG. 2 shows an exemplary alternative end effector (100) that may be used in place of end effector (40) described above, such that end effector (100) may be readily incorporated into instrument (10). End effector (100) of this example comprises a clamp arm (120) and an ultrasonic blade (130). Ultrasonic blade (130) is substantially similar to ultrasonic blade (42) described above. Clamp arm (120) is pivotally coupled with an outer tube (110) at a pivot coupling (124). Outer tube (110) may be provided as a component of shaft assembly (30). A rod (126) is pivotally coupled with clamp arm (120) and is translatable to selectively pivot clamp arm (120) toward and away from ultrasonic blade (130). Rod (126) may be actuated by trigger (28) and/or any other suitable user input feature. Rod (126) may also be substituted with a cable, beam, and/or any other suitable structure. Various other ways in which clamp arm (120) may be actuated to selectively pivot toward and away from ultrasonic blade (130) will be apparent to those of ordinary skill in the art in view of the teachings herein.

Figure 3:
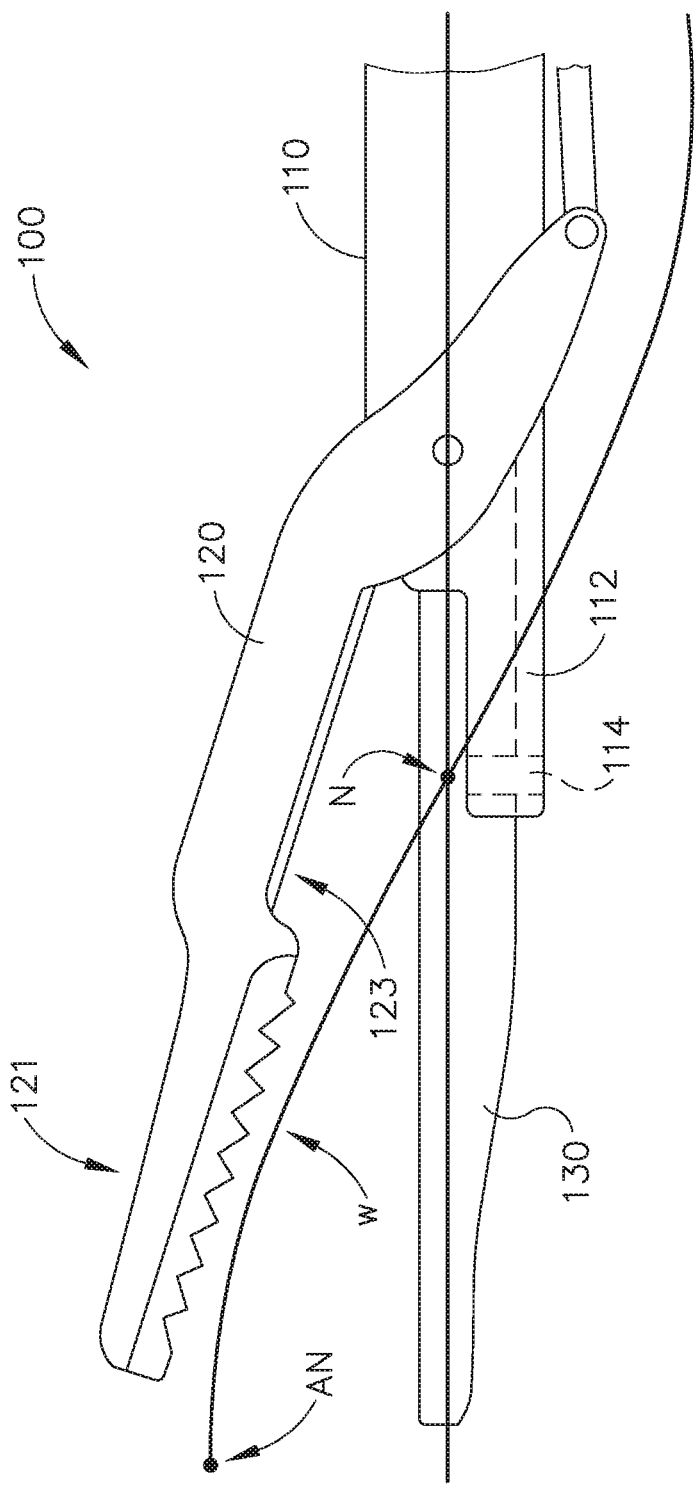
FIG. 3 depicts a partial side elevational view of the end effector of FIG. 2, with a harmonic wave superimposed to show exemplary nodal positioning.

Outer tube (110) includes a distally projecting tongue (112), which further includes a blade support (114). Blade support (114) comprises a pad that engages ultrasonic blade (130) at a position corresponding to a node associated with resonant ultrasonic vibrations communicated through ultrasonic blade (130). This is illustrated in FIG. 3, which shows a wave (W) depicting the resonant ultrasonic vibrations communicated through ultrasonic blade (130), with a node (N) being at the same longitudinal position as blade support (114). The rest of tongue (112) does not contact ultrasonic blade (130); yet tongue (112) extends around a substantial portion of the underside exterior of ultrasonic blade (130). Tongue (112) thus serves as a partial shield, preventing tissue from contacting the shielded portion of ultrasonic blade (130).

Clamp arm (120) includes a fast cutting region (121) and a slow cutting region (123), which is proximal to fast cutting region (121). In the present example, fast cutting region (121) is more effective for cutting tissue (through a shearing action); while slow cutting region (123) is more effective for sealing tissue (through a clamping action). Slow cutting region (123) includes a tissue pad (122), which extends along the full length of slow cutting region (123) and thus serves to demarcate slow cutting region (123). By way of example only, tissue pad (122) may comprise polytetrafluoroethylene and/or any other suitable material(s); and/or may be configured in accordance with at least some of the teachings of U.S. Pub. No. 2006/0079874, the disclosure of which is incorporated by reference herein. In the present example, tissue pad (122) is configured such that tissue will be clamped along a horizontal plane between tissue pad (122) and ultrasonic blade (130), without pad (122) or blade (130) passing through that horizontal plane. However, and as will be described in greater detail below in reference to FIGS. 5-9, fast cutting region (121) is configured such that tissue will be clamped obliquely between fast cutting region (121) and ultrasonic blade (130), with fast cutting region and ultrasonic blade (130) passing through the same horizontal plane in a cross-bite type of arrangement to provide oblique shearing of tissue.

As can be seen in FIG. 2, blade support (114) is at a longitudinal position corresponding to the longitudinal center of slow cutting region (123) when clamp arm (120) is pivoted to a closed position against ultrasonic blade (130). It should therefore be understood that slow cutting region (123) is centered about a node (N) associated with resonant ultrasonic vibrations communicated through ultrasonic blade (130). In some other versions, the node (N) is proximal to slow cutting region. For instance, the node (N) may be located proximal to pivotal coupling (124). As yet another merely illustrative variation, a first node (N) may be located at the proximal end of slow cutting region (123), with a second node (N) being located at the distal end of slow cutting region (123) (i.e., at the transition between regions (121, 123)).

In the present example, and as best seen in FIG. 3, the distal tip of ultrasonic blade (130) is located at a longitudinal position corresponding to an anti-node (AN) associated with resonant ultrasonic vibrations communicated through ultrasonic blade (130). Clamp arm (120) distally terminates at approximately the same longitudinal position as ultrasonic blade (130) when clamp arm (120) is pivoted to a closed position against ultrasonic blade (130). It should therefore be understood that fast cutting region (121) is located in a region closest to anti-node (AN) associated with resonant ultrasonic vibrations communicated through ultrasonic blade (130). When using end effector (100) to sever and seal tissue, the operator may position the tissue between slow cutting region (123) and ultrasonic blade (130) if the tissue is relatively thick; or between fast cutting region (121) and ultrasonic blade (130) if the tissue is relatively thin and the operator wishes to provide a relatively fast cutting speed.

Figure 4:
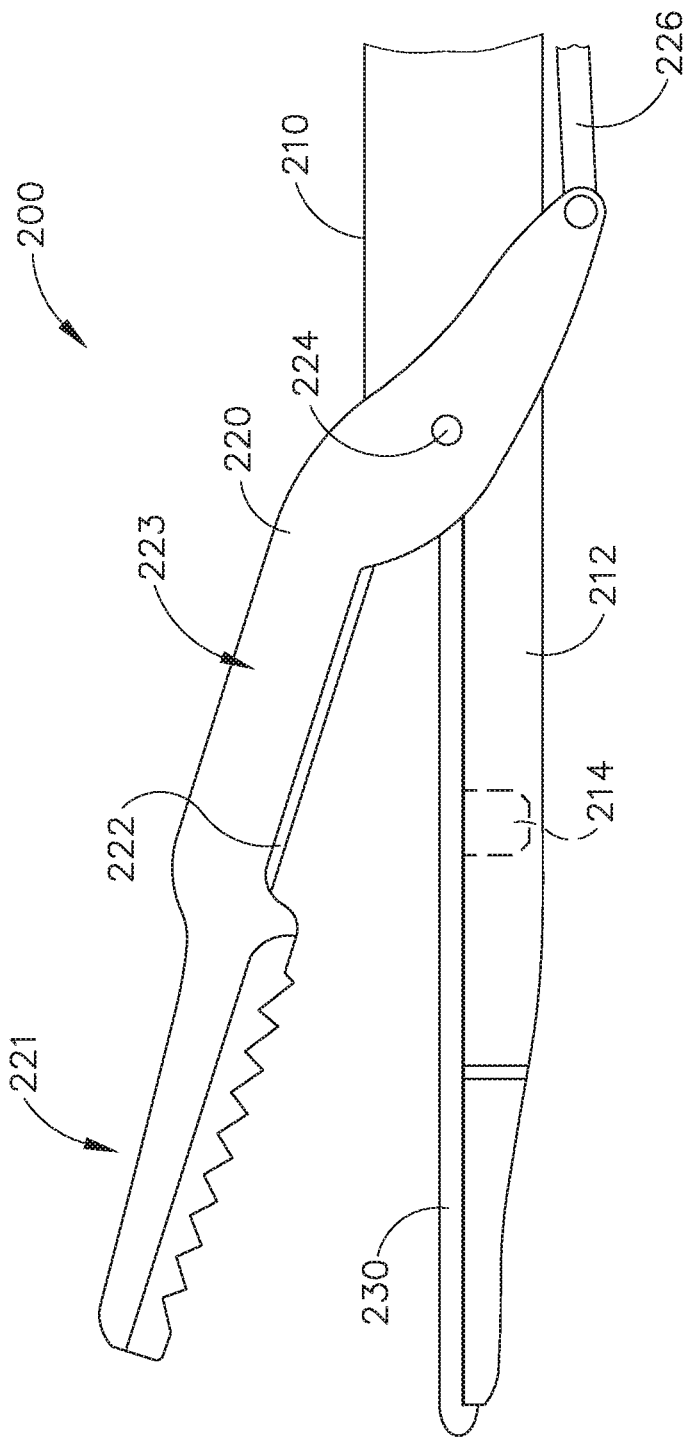
FIG. 4 depicts a partial side elevational view of another exemplary alternative end effector suitable for incorporation in the instrument of FIG. 1.

FIG. 4 shows another exemplary alternative end effector (200) that may be used in place of end effector (40) described above, such that end effector (200) may be readily incorporated into instrument (10). End effector (200) of this example comprises a clamp arm (220) and an ultrasonic blade (230). Ultrasonic blade (230) is substantially similar to ultrasonic blades (42, 130) described above. Clamp arm (220) is substantially similar to clamp arm (120) described above. In particular, clamp arm (220) includes a fast cutting region (221), a slow cutting region (223), a tissue pad (222), a pivotal coupling (224), and a rod (226). These components are substantially similar to fast cutting region (U1), slow cutting region (123), tissue pad (122), pivotal coupling (124), and rod (126), respectively, as described above. Outer tube (210) of this example is also similar to outer tube (110) described above, except that tongue (212) of outer tube (210) projects further distally than tongue (112) of outer tube (110). In particular, tongue (212) extends to a longitudinal position corresponding to the distal tip of ultrasonic blade (230). This simply provides additional shielding to the underside of ultrasonic blade (230). Tongue (212) also includes a blade support (214), though this is substantially similar to blade support (113) described above. In some instances, at least part of tongue (212) is configured in accordance with at least some of the teachings of U.S. Pub. No. 2012/0029546, now U.S. Pat. No. 8,591,536, issued on Nov. 26, 2013, the disclosure of which is incorporated by reference herein.

Figure 5:
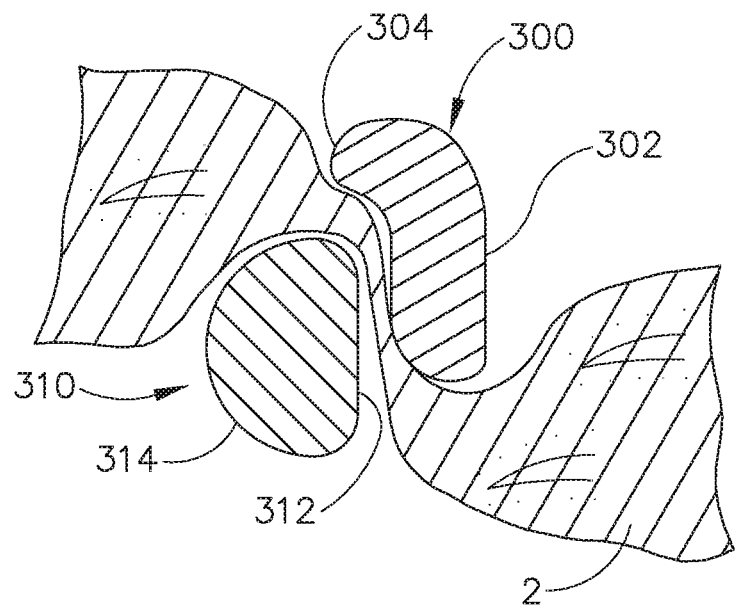
FIG. 5 depicts a cross-sectional view of an exemplary configuration of an end effector, taken along line A-A of FIG. 2, clamping tissue.

FIGS. 5-9 show exemplary alternative forms that the fast cutting sections (121, 221) of end effectors (100, 200) may take. In particular, FIG. 5 shows a clamp arm (300) and ultrasonic blade (310) clamping tissue (2) along a non-horizontal path. Clamp arm (300) and ultrasonic blade (310) are not centered along a common vertical axis in this example; yet they pass through a common horizontal plane in this example. Clamp arm (300) includes a substantially vertical portion (302) and a substantially transverse portion (304), which projects laterally to cross a vertical plane that is interposed between vertical portion (302) and ultrasonic blade (310). Transverse portion (304) is positioned above substantially vertical portion (302) in this example. Ultrasonic blade (310) has a substantially vertical face (312) and a rounded face (314), such that ultrasonic blade (310) has a reverse D-shaped cross-sectional profile. When tissue (2) is clamped between clamp arm (300) and ultrasonic blade (310), tissue (2) is captured between substantially vertical portion (302) of clamp arm (300) and substantially vertical face (312) of ultrasonic blade (310). Tissue (2) is also captured between substantially transverse portion (304) of clamp arm (300) and the upper region of rounded face (314). Clamp arm (300) and ultrasonic blade (310) may cooperate to provide a shearing action against tissue (2) as clamp arm (300) is pivoted toward ultrasonic blade (310).

Figure 6:
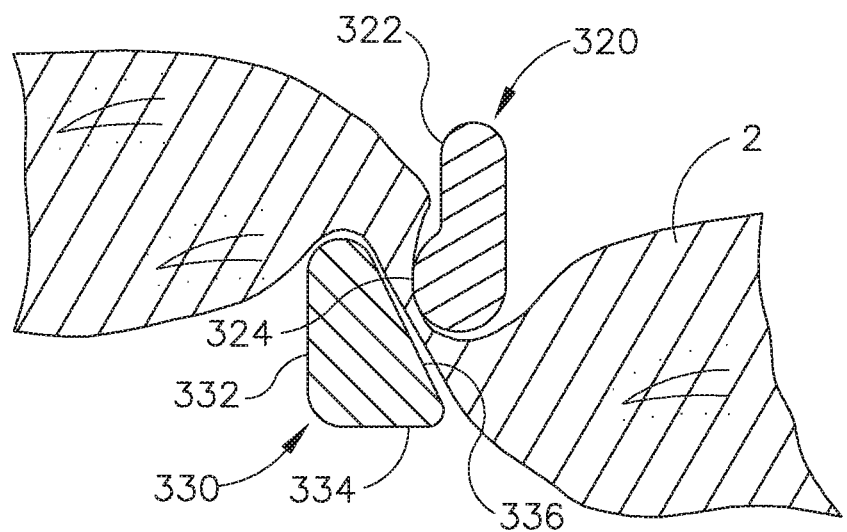
FIG. 6 depicts a cross-sectional view of another exemplary configuration of an end effector, taken along line A-A of FIG. 2, clamping tissue.

FIG. 6 shows another clamp arm (320) and ultrasonic blade (330) clamping tissue (2) along a non-horizontal path. Clamp arm (320) and ultrasonic blade (330) are not centered along a common vertical axis in this example; yet they pass through a common horizontal plane in this example. Clamp arm (320) includes a substantially vertical portion (322) and a substantially transverse portion (324), which projects laterally to cross a vertical plane that is interposed between vertical portion (322) and ultrasonic blade (330). Transverse portion (324) is positioned below substantially vertical portion (322) in this example. Ultrasonic blade (330) has a substantially vertical face (332), a substantially horizontal face (334), and an oblique face (336), such that ultrasonic blade (330) has a cross-sectional profile similar to a right triangle. When tissue (2) is clamped between clamp arm (320) and ultrasonic blade (330), tissue (2) is captured between transverse portion (324) of clamp arm (320) and oblique face (336) of ultrasonic blade (330). Clamp arm (320) and ultrasonic blade (330) may cooperate to provide a shearing action against tissue (2) as clamp arm (320) is pivoted toward ultrasonic blade (330).

Figure 7:
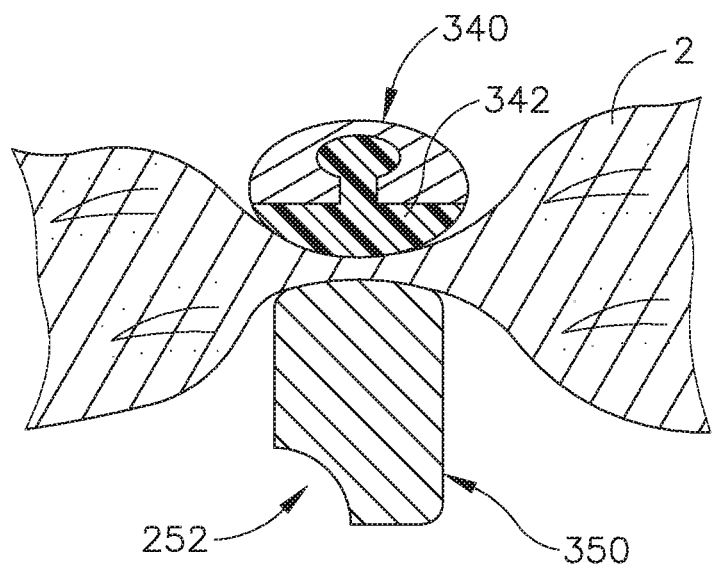
FIG. 7 depicts a cross-sectional view of another exemplary configuration of an end effector, taken along line A-A of FIG. 2, clamping tissue.

FIG. 7 shows another clamp arm (340) and ultrasonic blade (350) clamping tissue (2), this time along a horizontal path. Clamp arm (340) and ultrasonic blade (350) are both centered along a common vertical axis in this example. Clamp arm (340) includes a tissue pad (342) similar to tissue pads (122, 222) described above. Tissue pad (342) is positioned below clamp arm (340) such that tissue pad (342) includes a downwardly presented surface. Clamp arm (340) and tissue pad (342) together define a generally elliptical cross-sectional profile. Ultrasonic blade (350) has a generally rectangular cross-sectional profile, with a notch (352) extending along a lower corner. When tissue (2) is clamped between clamp arm (340) and ultrasonic blade (330), tissue (2) is captured between tissue pad (342) and the upper surface of ultrasonic blade (350).

Figure 8:
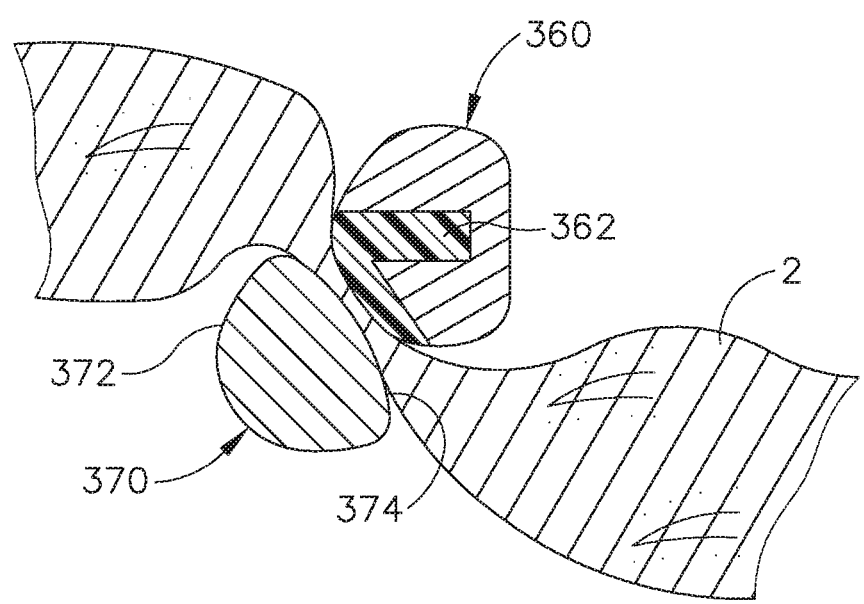
FIG. 8 depicts a cross-sectional view of another exemplary configuration of an end effector, taken along line A-A of FIG. 2, clamping tissue.

FIG. 8 shows another clamp arm (360) and ultrasonic blade (370) clamping tissue (2) along a non-horizontal path. Clamp arm (360) and ultrasonic blade (370) are not centered along a common vertical axis in this example; yet they pass through a common horizontal plane in this example. Clamp arm (360) includes a tissue pad (362) similar to tissue pads (122, 222) described above. Tissue pad (362) is positioned on a lateral side of clamp arm (360), such that tissue pad (362) presents an oblique exposed contact surface associated with the lower left-hand quadrant of clamp arm (360). Ultrasonic blade (370) includes a rounded surface (372) and an oblique surface (374), such that ultrasonic blade (370) has an angled D-shaped cross-sectional profile. When tissue (2) is clamped between clamp arm (360) and ultrasonic blade (370), tissue (2) is captured between the oblique exposed surface of tissue pad (362) and oblique surface (374) of ultrasonic blade (370). Clamp arm (360) and ultrasonic blade (370) may cooperate to provide a shearing action against tissue (2) as clamp arm (360) is pivoted toward ultrasonic blade (370).

Figure 9:
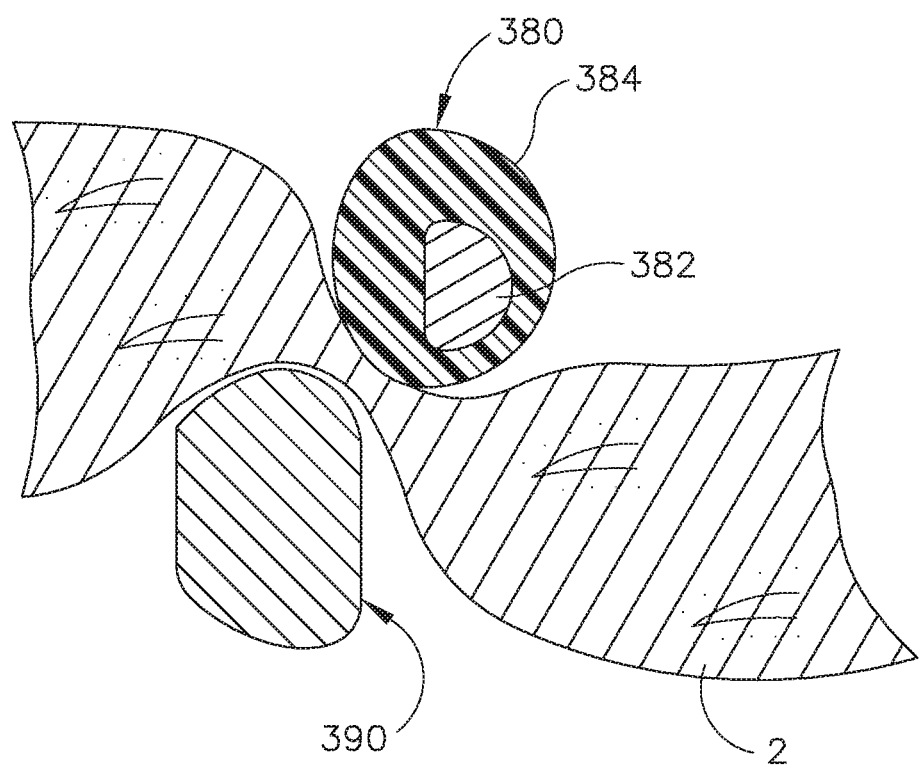
FIG. 9 depicts a cross-sectional view of another exemplary configuration of an end effector, taken along line A-A of FIG. 2, clamping tissue.

FIG. 9 shows another clamp arm (380) and ultrasonic blade (390) clamping tissue (2) along a non-horizontal path. Clamp arm (380) and ultrasonic blade (390) are not centered along a common vertical axis in this example; yet they pass through a common horizontal plane in this example. Clamp arm (380) includes a spine portion (382) and a pad sleeve (384) encompassing spine portion (382). Clamp arm (380) has a generally round cross-sectional configuration. Ultrasonic blade (390) has a generally rectangular cross-sectional configuration. When tissue (2) is clamped between clamp arm (380) and ultrasonic blade (390), tissue (2) is captured between an upper corner of ultrasonic blade (390) and clamp arm (380). Clamp arm (380) and ultrasonic blade (390) may cooperate to provide a shearing action against tissue (2) as clamp arm (380) is pivoted toward ultrasonic blade (390).

While FIGS. 5-9 have been described above as showing exemplary alternative forms that the fast cutting sections (121, 221) of end effectors (100, 200) may take, it should be understood that slow cutting sections (123, 223) of end effectors (100, 200) may also take any of the various forms shown in FIGS. 5-9. Furthermore, the forms shown FIGS. 4-9 may be readily varied in numerous ways. Other suitable configurations for fast cutting sections (121, 221) and/or slow cutting sections (123, 223) will be apparent to those of ordinary skill in the art in view of the teachings herein.

Figure 10:
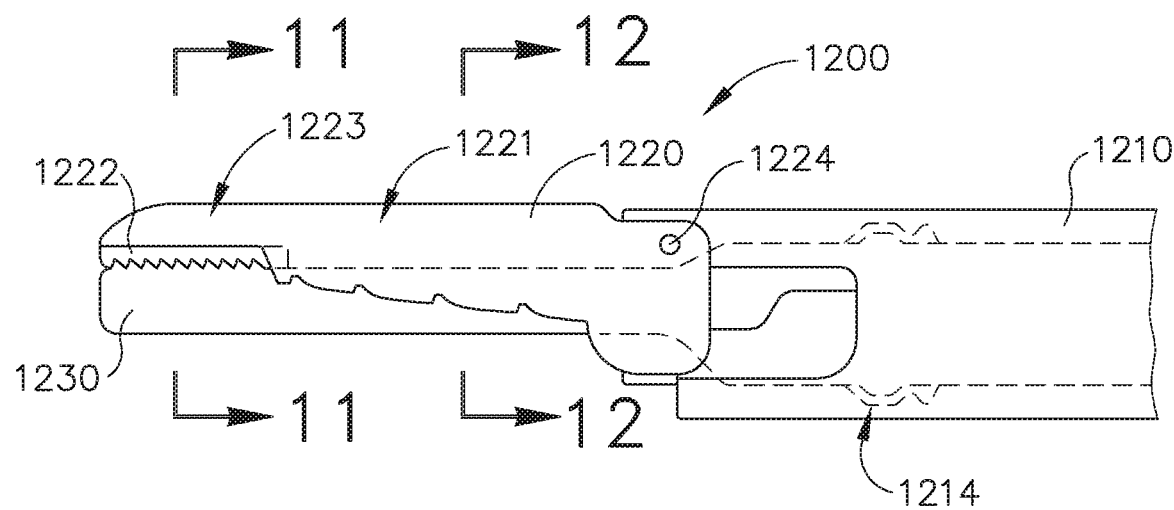
FIG. 10 depicts a partial side elevational view of another exemplary alternative end effector suitable for incorporation in the instrument of FIG. 1.
Figure 11:
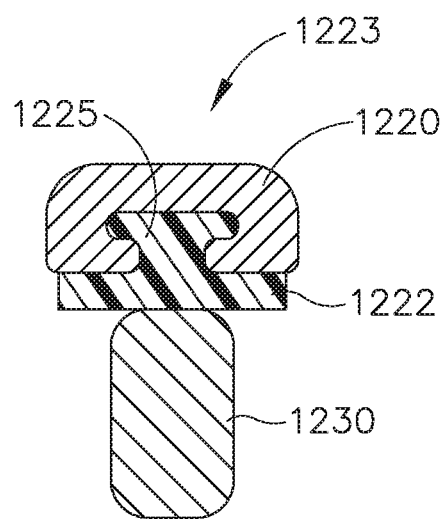
FIG. 11 depicts a cross-sectional view of the end effector of FIG. 10, taken along line 11-11 of FIG. 10.
Figure 12:
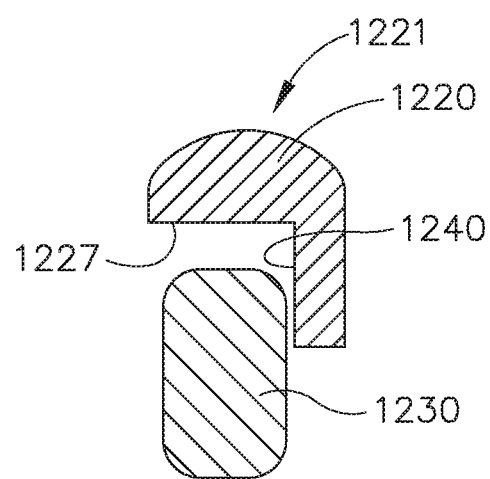
FIG. 12 depicts a cross-sectional view of the end effector of FIG. 10, taken along line 12-12 of FIG. 10.

FIGS. 10-12 show yet another exemplary alternative end effector (1200) that may be used in place of end effector (40) described above, such that end effector (1200) may be readily incorporated into instrument (10). End effector (1200) of this example comprises an outer tube (1210), a pivoting clamp arm (1220), and an ultrasonic blade (1230). Ultrasonic blade (1230) is substantially similar to ultrasonic blades (42, 130) described above. Clamp arm (1220) is substantially similar to clamp arm (120) described above. In particular, clamp arm (1220) includes a fast cutting region (1221), a slow cutting region (1223), a tissue pad (1222), and a pivotal coupling (1224). However, in this example the longitudinal positioning of fast cutting region (1221) and a slow cutting region (1223) is reversed compared to the longitudinal positioning of fast cutting region (121) and a slow cutting region (123). In particular, fast cutting region (1221) is positioned proximal to slow cutting region (1223) in this example. This may provide a configuration that is roughly similar to the configuration provided by a Foster-Gilles needle holder. The configuration may thus provide some degree of familiarity to some operators.

As shown in FIG. 11, the portion of clamp arm (1220) extending through slow cutting region (1223) is substantially flat and generally symmetric about a vertical plane that extends along the longitudinal axis of end effector (1200). Tissue pad (1222) is fitted in clamp arm (1220) by a rail (1225), though it should be understood that numerous other relationships may be used. By way of example only, tissue pad (1222) may comprise polytetrafluoroethylene and/or any other suitable material(s); and/or may be configured in accordance with at least some of the teachings of U.S. Pub. No. 2006/0079874, now abandoned, the disclosure of which is incorporated by reference herein. In the present example, tissue pad (1222) is configured such that tissue will be clamped along a horizontal plane between tissue pad (1222) and ultrasonic blade (1230), without pad (1222) or blade (1230) passing through that horizontal plane.

As shown in FIG. 12, the portion of clamp arm (1220) extending through fast cutting region (1221) is generally L-shaped and asymmetric about a vertical plane that extends along the longitudinal axis of end effector (1200). In particular, this portion of clamp arm (1220) includes a horizontally extending portion (1227) positioned above ultrasonic blade (1230) and a vertically extending portion (1240) positioned lateral to ultrasonic blade (1230). Horizontally extending portion (1227) crosses over a vertical plane that extends along the longitudinal axis of end effector (1200); while vertically extending portion (1240) is positioned lateral to that same vertical plane. When tissue is clamped between the portion of clamp arm (1220) extending through fast cutting region (1221) and ultrasonic blade (1230), clamp arm (1220) and ultrasonic blade (1230) may cooperate to provide a shearing action against the tissue as clamp arm (1220) is pivoted toward ultrasonic blade (1230).

Ultrasonic blade (1230) is coupled with outer tube (1210) at a blade support (1214) located proximal to pivotal coupling (1224). Blade support (1214) is at a longitudinal position corresponding to a node associated with resonant ultrasonic vibrations communicated through ultrasonic blade (1230). In the present example, the distal end of end effector (1200) terminates at a longitudinal position corresponding to an anti-node associated with resonant ultrasonic vibrations communicated through ultrasonic blade (1230). In some versions, there are no nodes positioned anywhere along the length of ultrasonic blade (1230) between blade support (1214) and the distal tip of end effector (1200). In some other versions, clamp arm (1220) is configured such that a node is located at the transition between fast cutting region (1221) and slow cutting region (1223), in addition to having a separate node at blade support (1214). As yet another merely illustrative example, clamp arm (1220) may be configured such that a node is located at the center of slow cutting region (1223), in addition to having a separate node at blade support (1214). Still other suitable configurations and relationships between features of end effector (1200) and the waveform of resonant ultrasonic vibrations communicated through ultrasonic blade (1230) will be apparent to those of ordinary skill in the art in view of the teachings herein.

Figure 15:
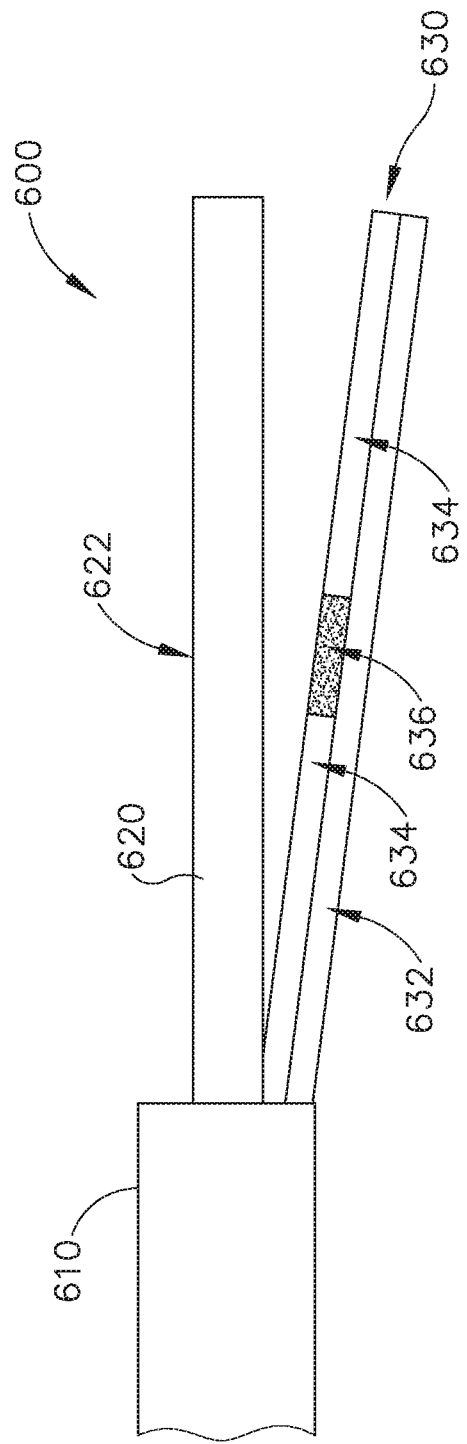
FIG. 15 depicts a partial side elevational view of another exemplary alternative end effector suitable for incorporation in the instrument of FIG. 1.

III. Exemplary Alternative Ultrasonic End Effector with Heat Generating Pad Insert It should be understood that the degree of longitudinal displacement in an ultrasonically vibrating blade will vary along the length of the blade, with the displacement being the greatest at a position corresponding to an anti-node; and with the displacement being reduced to zero at a position corresponding to a node. The active length of an ultrasonic blade, such as ultrasonic blade (42), may be defined from the distal tip of the blade (which may be associated with an anti-node) to the point on the blade where the longitudinal displacement (through ultrasonic vibrations) decreases to 50%. This active length may represent a length corresponding to less than a quarter of a wavelength associated with ultrasonic vibrations being communicated along the blade. Thus, the region of length around a position corresponding to a node associated with ultrasonic vibrations being communicated long the blade may be viewed as an acoustic cold spot or a nodal gap where it is difficult for the blade to quickly develop heat to cut and coagulate tissue. It may therefore be desirable to avoid such cold spots (i.e., bridge the nodal gap), to thereby effectively extend the active length of the ultrasonic blade. Merely illustrative examples of end effectors that effectively extend the effective length of an ultrasonic blade are shown in FIGS. 13-15 and are described in greater detail below; while other variations will be apparent to those of ordinary skill in the art in view of the teachings herein.

At least some of the examples described below rely on the property of absolute or dynamic viscosity, which is observed in a mechanical system where a moving plate slides across a stationary plate with a lubricant between the two. The value for absolute viscosity can be expressed as $\eta=Fh/Av$; where $\eta$ is the absolute viscosity; F is the friction force between the moving plate and the lubricant; h is the distance between the moving plate and the stationary plate; A is the contact area between the moving plate and the lubricant; and v is the velocity of the moving plate. The temperature increase between the two plates is a function of the absolute viscosity $\eta$. In the context of an ultrasonic surgical instrument (10), ultrasonic blade (42) may serve as the moving plate, clamp arm (40) may serve as the stationary plate, and the tissue between blade (42) and arm (40) may serve as the lubricant. The nodal gap could be bridged by keeping absolute viscosity $\eta$ constant along the desired working length of ultrasonic blade (42), thereby keeping a substantially constant temperature along the desired working length of ultrasonic blade (42) to effectively eliminate what would otherwise be an acoustic cold spot. In a conventional version of instrument (10), the velocity v decreases in the nodal gap associated with the acoustic cold spot referred to above. Thus, in order to maintain a constant absolute viscosity $\eta$ across the nodal gap (to thereby eliminate the acoustic cold spot and provide uniform heating of tissue), it may be desirable to affect one or more of the other variables to effectively compensate for the reduction in velocity v. One or more of the examples described below may effectively compensate for the reduction in velocity v by effectively increasing the contact area A as described below. T One or more of the examples described below may effectively compensate for the reduction in velocity v by effectively decreasing the tissue height h as described below. One or more of the examples described below may effectively compensate for the reduction in velocity v by increasing the friction F by increasing the coefficient of friction in the tissue pad at the nodal region.

FIG. 13 shows an exemplary alternative end effector (400) that may be used in place of end effector (40) described above, such that end effector (400) may be readily incorporated into instrument (10). End effector (400) of this example comprises an ultrasonic blade (420) extending distally from a shaft assembly (410). Ultrasonic blade (420) and shaft assembly (410) are substantially identical to ultrasonic blade (42) and shaft assembly (30) described above. End effector (400) also includes a clamp arm (430), which is selectively pivotable toward and away from ultrasonic blade (420) similar to clamp arm (44) described above. Clamp arm (430) includes a metallic arm (432) section, a pair of polytetrafluoroethylene pads (434), and a polyimide pad (436) positioned between polytetrafluoroethylene pads (434). Polyimide pad (436) is located at a position along clamp arm (430) that corresponds to the location (422) of a node associated with resonant ultrasonic vibrations communicated through ultrasonic blade (420). Polyimide is provided as an exemplary material for pad (436) because polyimide has a higher melting temperature and higher coefficient of friction than polytetrafluoroethylene. It should be understood, however, that numerous other suitable materials may be used for pad (436), including any suitable material that has a higher melting temperature and/or higher coefficient of friction than polytetrafluoroethylene.

Due to the differences in the material properties of polytetrafluoroethylene and polyimide, polyimide pad (436) may tend to generate higher heat when forced against an active ultrasonic blade (420). Thus, when tissue is clamped between clamp arm (430) and ultrasonic blade (420), and ultrasonic blade (420) is activated, the ultrasonic vibrations communicated by blade (420) immediately adjacent to the nodal location (422) may be more effectively carried by polyimide pad (436) than they would otherwise be carried by a polytetrafluoroethylene pad that would otherwise extend across the nodal location (422). In other words, due to the material properties and location of polyimide pad (436), polyimide pad (436) may effectively bridge the nodal gap and effectively eliminate the acoustic cold spot by providing substantially constant heating along the length of clamp arm (430).

FIG. 14 shows another exemplary alternative end effector (500) that may be used in place of end effector (40) described above, such that end effector (500) may be readily incorporated into instrument (10). End effector (500) of this example comprises an ultrasonic blade (520) extending distally from a shaft assembly (510). Ultrasonic blade (520) and shaft assembly (510) are substantially identical to ultrasonic blade (42) and shaft assembly (30) described above. End effector (500) also includes a clamp arm (530), which is selectively pivotable toward and away from ultrasonic blade (520) similar to clamp arm (44) described above. Clamp arm (530) includes a metallic arm section (532), a polytetrafluoroethylene pad (534), and a polyimide pad (536) positioned on polytetrafluoroethylene pad (534). Polyimide pad (536) is located at a position along clamp arm (530) that corresponds to the location (522) of a node associated with resonant ultrasonic vibrations communicated through ultrasonic blade (520). Polyimide is provided as an exemplary material for pad (536) because polyimide has a higher melting temperature and higher coefficient of friction than polytetrafluoroethylene. It should be understood, however, that numerous other suitable materials may be used for pad (536), including any suitable material that has a higher melting temperature and/or higher coefficient of friction than polytetrafluoroethylene.

The configuration of clamp arm (530) is similar to the configuration of claim arm (530) as described above, such that the material properties and location of polyimide pad (536) may result in polyimide pad (536) effectively bridging the nodal gap and effectively eliminating an acoustic cold spot by providing substantially constant heating along the length of clamp arm (530). However, in this example, polyimide pad (536) is raised relative to polytetrafluoroethylene pad (534). This creates additional interference against tissue when tissue is clamped between clamp arm (530) and ultrasonic blade (520). This additional interference may provide enhanced heating of the tissue, thereby further bridging the nodal gap.

FIG. 15 shows another exemplary alternative end effector (600) that may be used in place of end effector (40) described above, such that end effector (600) may be readily incorporated into instrument (10). End effector (600) of this example comprises an ultrasonic blade (620) extending distally from a shaft assembly (610). Ultrasonic blade (620) and shaft assembly (610) are substantially identical to ultrasonic blade (42) and shaft assembly (30) described above. End effector (600) also includes a clamp arm (630), which is selectively pivotable toward and away from ultrasonic blade (620) similar to clamp arm (44) described above. Clamp arm (630) includes a metallic arm (632) section, a pair of polytetrafluoroethylene pads (634), and a polyimide pad (636) positioned between polytetrafluoroethylene pads (634). Polyimide pad (636) is located at a position along clamp arm (630) that is slightly offset from the location (622) of a node associated with resonant ultrasonic vibrations communicated through ultrasonic blade (620). Polyimide is provided as an exemplary material for pad (636) because polyimide has a higher melting temperature and higher coefficient of friction than polytetrafluoroethylene. It should be understood, however, that numerous other suitable materials may be used for pad (636), including any suitable material that has a higher melting temperature and/or higher coefficient of friction than polytetrafluoroethylene. The offset of polyimide pad (636) in this example may provide a more desirable closing of the nodal gap than the version shown in FIG. 13. For instance, in some settings, it may be desirable to substantially close the nodal gap but not to close it completely uniformly. Various suitable lengths, widths, thicknesses, stand-off heights, nodal offsets, and materials that may be used for polyimide pads (436, 536, 636) will be apparent to those of ordinary skill in the art in view of the teachings herein.

IV. Exemplary Alternative Ultrasonic End Effector with Scalpel Extension

In some instances, an operator may wish to clamp tissue between a clamp arm and an ultrasonic blade to provide simultaneous severing and sealing of the clamped tissue. In some other instances, an operator may wish to use an ultrasonic blade like a scalpel, simultaneously severing and sealing tissue (or just spot sealing tissue) without clamping on the tissue with a clamp arm. Conventional instrumentation may require use of separate instruments to perform clamping operations and scalpel operations. However, the examples below provide both kinds of operations in a single instrument. It should be understood that the below examples are mere examples, and that numerous variations will be apparent to those of ordinary skill in the art in view of the teachings herein.

Figure 16:
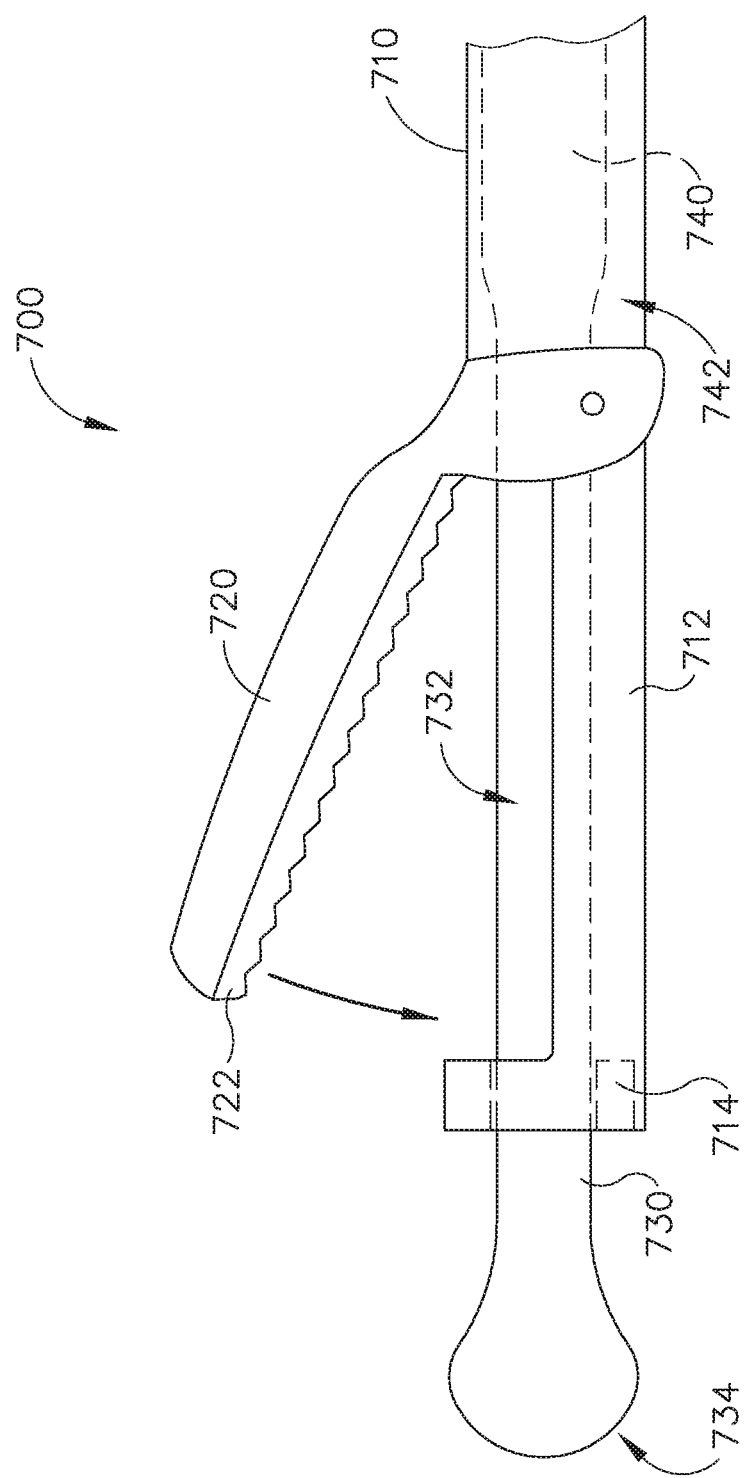
FIG. 16 depicts a partial side elevational view of another exemplary alternative end effector suitable for incorporation in the instrument of FIG. 1.

FIG. 16 shows another exemplary alternative end effector (700) that may be used in place of end effector (40) described above, such that end effector (700) may be readily incorporated into instrument (10). End effector (700) of this example comprises a clamp arm (720) and an ultrasonic blade (740). Ultrasonic blade (730) is substantially similar to ultrasonic blade (42) described above. Clamp arm (720) is pivotally coupled with an outer tube (710), which may be provided as a component of shaft assembly (30). Clamp arm (720) is pivotable toward and away from ultrasonic blade (730). Various suitable ways in which clamp arm (720) may be actuated to selectively pivot toward and away from ultrasonic blade (730) will be apparent to those of ordinary skill in the art in view of the teachings herein. Clamp arm (720) includes a tissue pad (722), which may comprise polytetrafluoroethylene and/or any other suitable material(s); and/or may be configured in accordance with at least some of the teachings of U.S. Pub. No. 2006/0079874, now abandoned, the disclosure of which is incorporated by reference herein.

Figure 17:
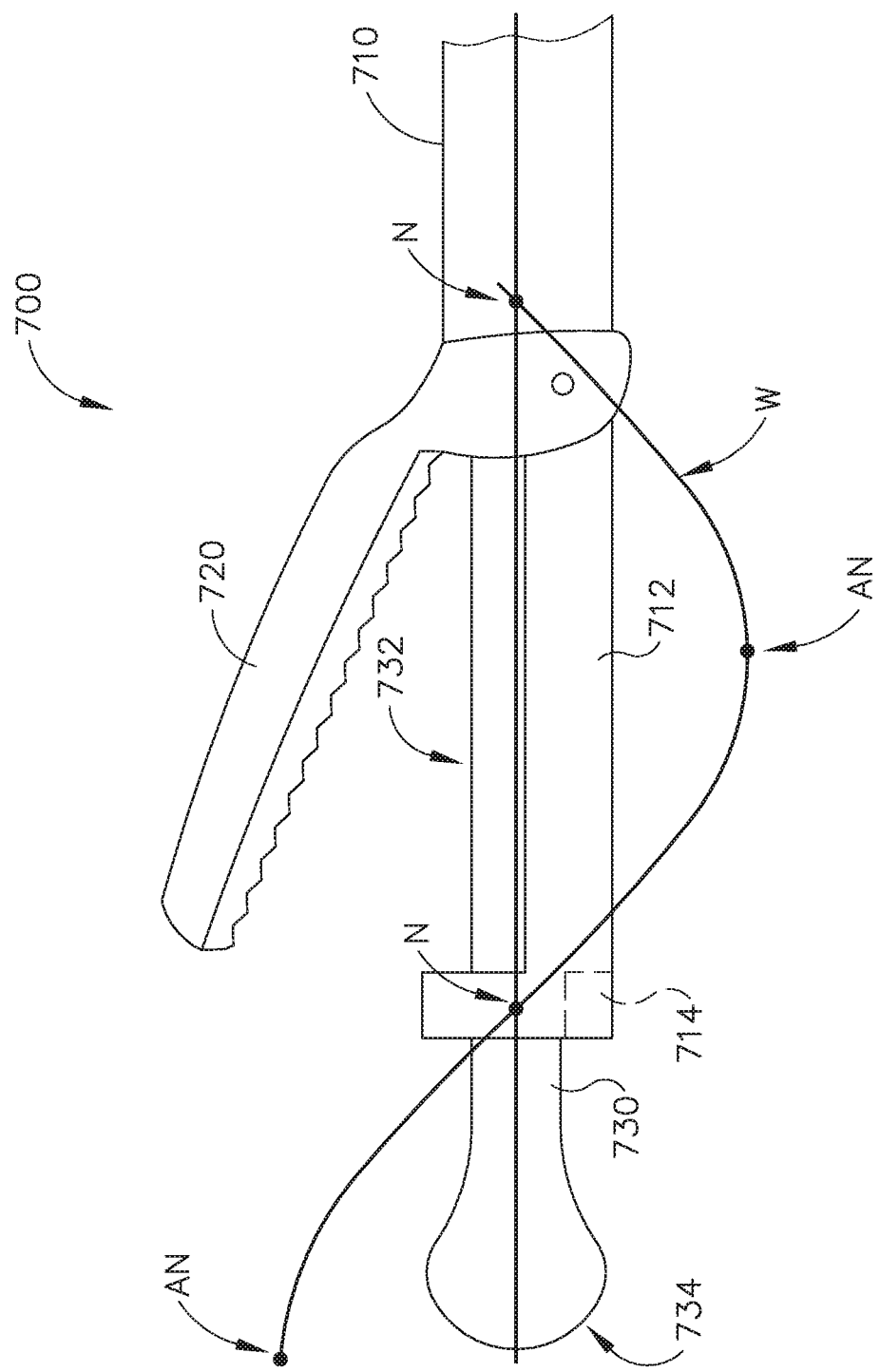
FIG. 17 depicts a partial side elevational view of the end effector of FIG. 16, with a harmonic wave superimposed to show exemplary nodal positioning.

Outer tube (710) includes a distally projecting tongue (712), which further includes a blade support (714). Blade support (714) comprises a pad that engages ultrasonic blade (730) at a position corresponding to a node associated with resonant ultrasonic vibrations communicated through ultrasonic blade (730). This is illustrated in FIG. 17, which shows a wave (W) depicting the resonant ultrasonic vibrations communicated through ultrasonic blade (730), with a node (N) being at the same longitudinal position as blade support (714). The rest of tongue (712) does not contact ultrasonic blade (730); yet tongue (712) extends around a substantial portion of the underside exterior of ultrasonic blade (730). Tongue (712) thus serves as a partial shield, preventing tissue from contacting the shielded portion of ultrasonic blade (730). Blade support (714) is located just distal to the distal end of clamp arm (720) when clamp arm (720) is clamped against ultrasonic blade (720). Blade support (714) thus provides a demarcation between a tissue clamping region (732) of ultrasonic blade (730) and a tissue scalpel region (734) of ultrasonic blade (730), which extends distally relative to blade support (714).

As best seen in FIG. 17, the distal tip of tissue scalpel region (734) is located at a position corresponding to an anti-node (AN) associated with resonant ultrasonic vibrations communicated through ultrasonic blade (730), such that tissue scalpel region (734) extends between a first anti-node (AN) and a first node (N). Tissue clamping region (732) extends between the first node (N) at blade support (714) and a second node (N), which is near the transition (742) from acoustic waveguide (740) to ultrasonic blade (730). Thus, it should be understood that a second anti-node (AN) is positioned at approximately the middle of tissue clamping region (732).

If an operator wishes to cut and seal tissue by clamping the tissue, the operator may simply position the tissue between clamp arm (720) and tissue clamping region of ultrasonic blade (730), actuate clamp arm (720) to clamp on the tissue, then activate ultrasonic blade (730) with ultrasonic vibrational energy. If the operator wishes to spot seal tissue or cut and seal tissue without clamping the tissue, the operator may simply engage the tissue with tissue scalpel region (734) and activate ultrasonic blade (730) with ultrasonic vibrational energy. Clamp arm (720) may remain in an open position as shown in FIG. 16 when the operator just uses tissue scalpel region (734). Alternatively, the operator may hold clamp arm (720) in a closed position, clamped down against tissue clamping region (732) of ultrasonic blade (730) during use of tissue scalpel region (734), even if no tissue is positioned between clamp arm (720) and tissue clamping region (732). Other suitable ways in which end effector (700) may be used will be apparent to those of ordinary skill in the art in view of the teachings herein.

Figure 18:
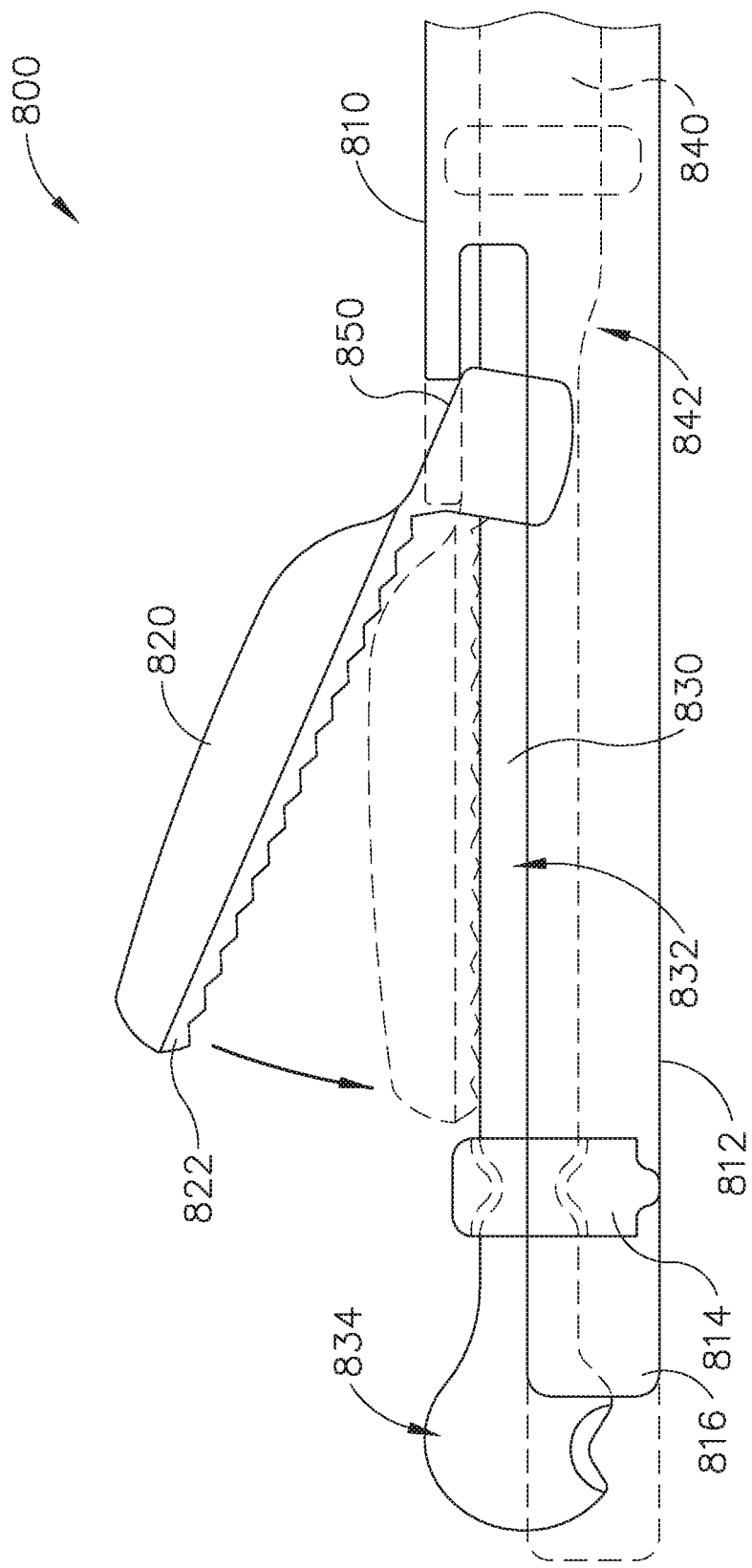
FIG. 18 depicts a partial side elevational view of another exemplary alternative end effector suitable for incorporation in the instrument of FIG. 1.

FIG. 18 shows another exemplary alternative end effector (800) that may be used in place of end effector (40) described above, such that end effector (800) may be readily incorporated into instrument (10). End effector (800) of this example comprises a clamp arm (820) and an ultrasonic blade (840). Ultrasonic blade (830) is substantially similar to ultrasonic blade (42) described above. Clamp arm (820) is pivotally coupled with an outer tube (810), which may be provided as a component of shaft assembly (30). Clamp arm (820) is pivotable toward and away from ultrasonic blade (830). In particular, outer tube (810) is configured to translate distally relative to ultrasonic blade (830) in order to pivot clamp arm (820) toward ultrasonic blade (830). Various suitable ways in which outer tube (810) may be actuated to selectively pivot clamp arm (820) toward and away from ultrasonic blade (830) will be apparent to those of ordinary skill in the art in view of the teachings herein. Clamp arm (820) includes a tissue pad (822), which may comprise polytetrafluoroethylene and/or any other suitable material(s); and/or may be configured in accordance with at least some of the teachings of U.S. Pub. No. 2006/0079874, now abandoned, the disclosure of which is incorporated by reference herein.

Outer tube (810) includes a distally projecting tongue (812), which further includes a blade support (814). Blade support (814) comprises a pad that engages ultrasonic blade (830) at a position corresponding to a node associated with resonant ultrasonic vibrations communicated through ultrasonic blade (830). The rest of tongue (812) does not contact ultrasonic blade (830); yet tongue (812) extends around a substantial portion of the underside exterior of ultrasonic blade (830). Tongue (812) thus serves as a partial shield, preventing tissue from contacting the shielded portion of ultrasonic blade (830). Blade support (814) is located just distal to the distal end of clamp arm (820) when clamp arm (20) is clamped against ultrasonic blade (820). Blade support (814) thus provides a demarcation between a tissue clamping region (832) of ultrasonic blade (830) and a tissue scalpel region (834) of ultrasonic blade (830), which extends distally relative to blade support (814). The distal tip of tissue scalpel region (834) is located at a position corresponding to an anti-node associated with resonant ultrasonic vibrations communicated through ultrasonic blade (830), such that tissue scalpel region (834) extends between a first anti-node and a first node. Tissue clamping region (832) extends between the first node at blade support (814) and a second node, which is near the transition (842) from acoustic waveguide (840) to ultrasonic blade (830). Thus, it should be understood that a second anti-node is positioned at approximately the middle of tissue clamping region (832).

Tongue (812) of the present example further includes a distal shield portion (816) that is distal to blade support (814) and that is operable to selectively shield at least part of tissue scalpel region (834) from tissue. In some instances, at least part of distal shield portion (816) is configured in accordance with at least some of the teachings of U.S. Pub. No. 2012/0029546, now U.S. Pat. No. 8,591,536, issued on Nov. 26, 2013, the disclosure of which is incorporated by reference herein. Tongue (812) is slidable with outer tube (810), such that shield portion (816) is operable to selectively shield or un-shield tissue, based on the longitudinal position of tongue (812) and outer tube (810). In some versions, outer tube (810) closes clamp arm (820) when outer tube (810) is in a distal position; and shield portion (816) also shields scalpel region (834) from tissue when outer tube (810) is in a distal position. Thus, shielding and clamping may occur substantially simultaneously. In some other versions, clamp arm (820) and shield portion (816) are actuated independently. Various suitable ways in which actuation of clamp arm (820) and actuation of shield portion (816) may be decoupled and be thereby independent will be apparent to those of ordinary skill in the art in view of the teachings herein. It should also be understood that blade support (814) may remain in a fixed longitudinal position while outer tube (820) and tongue (812) translate. For instance, blade support (814) may be secured to a fixed frame. Regardless, it should be understood that end effector (800) may be operated in substantially the same manner as end effector (700), as described above.

Figure 19:
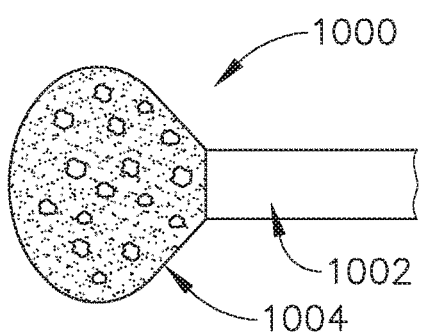
FIG. 19 depicts a partial side elevational view of an exemplary alternative ultrasonic blade suitable for incorporation in any of the end effectors referred to herein.
Figure 20:
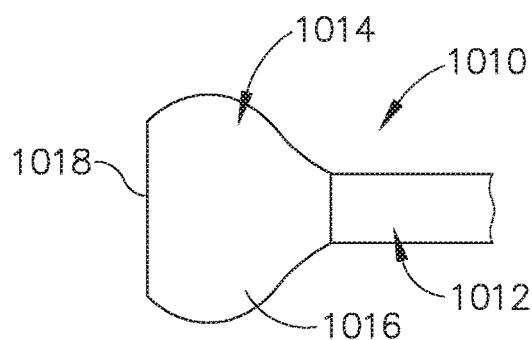
FIG. 20 depicts a partial side elevational view of another exemplary alternative ultrasonic blade suitable for incorporation in any of the end effectors referred to herein.
Figure 21:
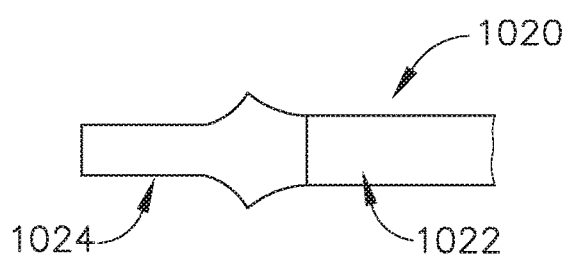
FIG. 21 depicts a partial top plan view of another exemplary alternative ultrasonic blade suitable for incorporation in any of the end effectors referred to herein.
Figure 22:
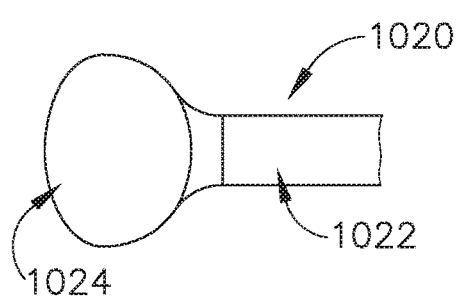
FIG. 22 depicts a partial side elevational view of the ultrasonic blade of FIG. 21.
Figure 23:
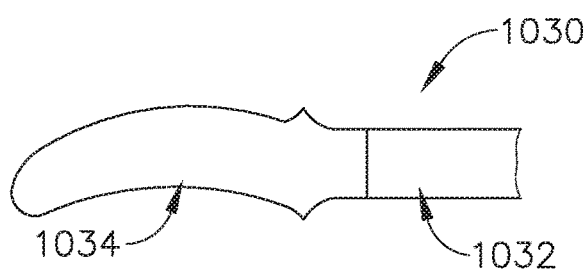
FIG. 23 depicts a partial top plan view of another exemplary alternative ultrasonic blade suitable for incorporation in any of the end effectors referred to herein.
Figure 24:
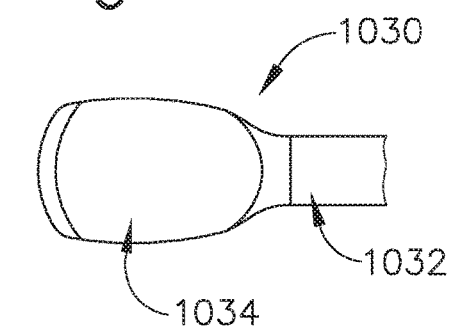
FIG. 24 depicts a partial side elevational view of the ultrasonic blade of FIG. 23.
Figure 25:
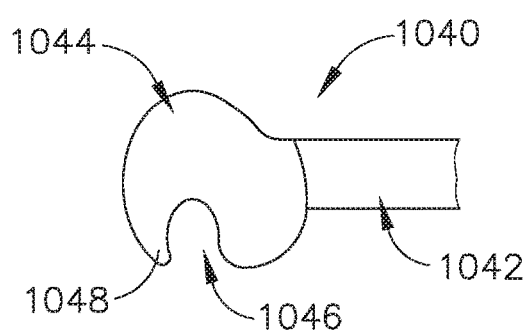
FIG. 25 depicts a partial top plan view of another exemplary alternative ultrasonic blade suitable for incorporation in any of the end effectors referred to herein.
Figure 26:
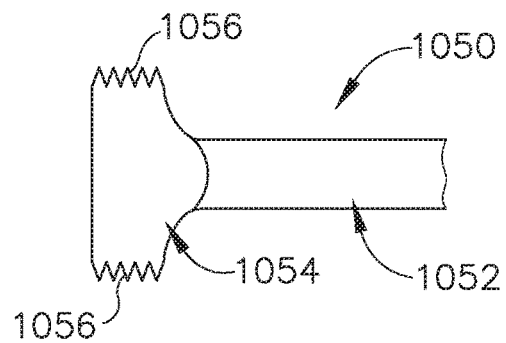
FIG. 26 depicts a partial top plan view of another exemplary alternative ultrasonic blade suitable for incorporation in any of the end effectors referred to herein.

FIGS. 19-26 show exemplary alternative forms that scalpel region (734, 834) of end effectors (700, 800) may take. In particular, FIG. 19 shows a distal end of an ultrasonic blade (1000) having a generally cylindraceous portion (1002) and a roughened tip (1004). Tip (1004) of this example is generally spherical and includes one or more of grit, recesses, or other protrusions to provide a rough exterior. FIG. 20 shows a distal end of an ultrasonic blade (1010) having a generally cylindraceous portion (1012) and a tip (1014) with a generally spherical section (1016) and a flat distal face (1018). FIGS. 21-22 show a distal end of an ultrasonic blade (1020) having a generally cylindraceous portion (1022) and a flattened, spatula-like section (1024). FIGS. 23-24 show a distal end of an ultrasonic blade (1030) having a generally cylindraceous portion (1032) and a curved, spatula-like section (1034). FIG. 25 shows a distal end of an ultrasonic blade (1040) having a generally cylindraceous portion (1042) and a tip (1044) with a laterally extending recess (1046) forming a hook (1048). FIG. 26 shows a distal end of an ultrasonic blade (1045) having a generally cylindraceous portion (1052) and a tip (1054) with a hammerhead configuration, including a pair of laterally presented serrated edges (1056). Of course, all of these configurations are merely illustrative. Still other suitable configurations will be apparent to those of ordinary skill in the art in view of the teachings herein.

V. Exemplary Alternative Ultrasonic End Effector with Tube Extension Pad

In ultrasonic instruments having a relatively long ultrasonic blade, there may be instances where the ultrasonic blade bends and deflects away from a longitudinal axis defined by the ultrasonic blade at rest. These deflections may occur when a clamp arm is pressing against the ultrasonic blade and/or when tissue is pressing against the ultrasonic blade. In some instances, these ultrasonic blade deflections may be undesirable. Having a relatively long ultrasonic blade might also increase the presence of nodal gaps, thereby increasing the prominence of acoustic cold spots as described above. It may be desirable to simultaneously address ultrasonic blade deflection and nodal gaps. An example of how this may be done will be described in greater detail below, while other examples will be apparent to those of ordinary skill in the art in view of the teachings herein.

FIGS. 27-32 show another exemplary alternative end effector (1100) that may be used in place of end effector (40) described above, such that end effector (1100) may be readily incorporated into instrument (10). End effector (1100) of this example comprises a clamp arm (1130) and an ultrasonic blade (1120). Ultrasonic blade (1120) is substantially similar to ultrasonic blade (42) described above. Clamp arm (1130) is pivotally coupled with an outer tube (1110), which may be provided as a component of shaft assembly (30). Clamp arm (1130) is pivotable toward and away from ultrasonic blade (1120). Various suitable ways in which clamp arm (1130) may be actuated to selectively pivot toward and away from ultrasonic blade (1120) will be apparent to those of ordinary skill in the art in view of the teachings herein. Clamp arm (1130) includes a metallic arm section (1132) and a tissue pad (1134), which may comprise polytetrafluoroethylene and/or any other suitable material(s); and/or may be configured in accordance with at least some of the teachings of U.S. Pub. No. 2006/0079874, now abandoned, the disclosure of which is incorporated by reference herein.

Figure 27:
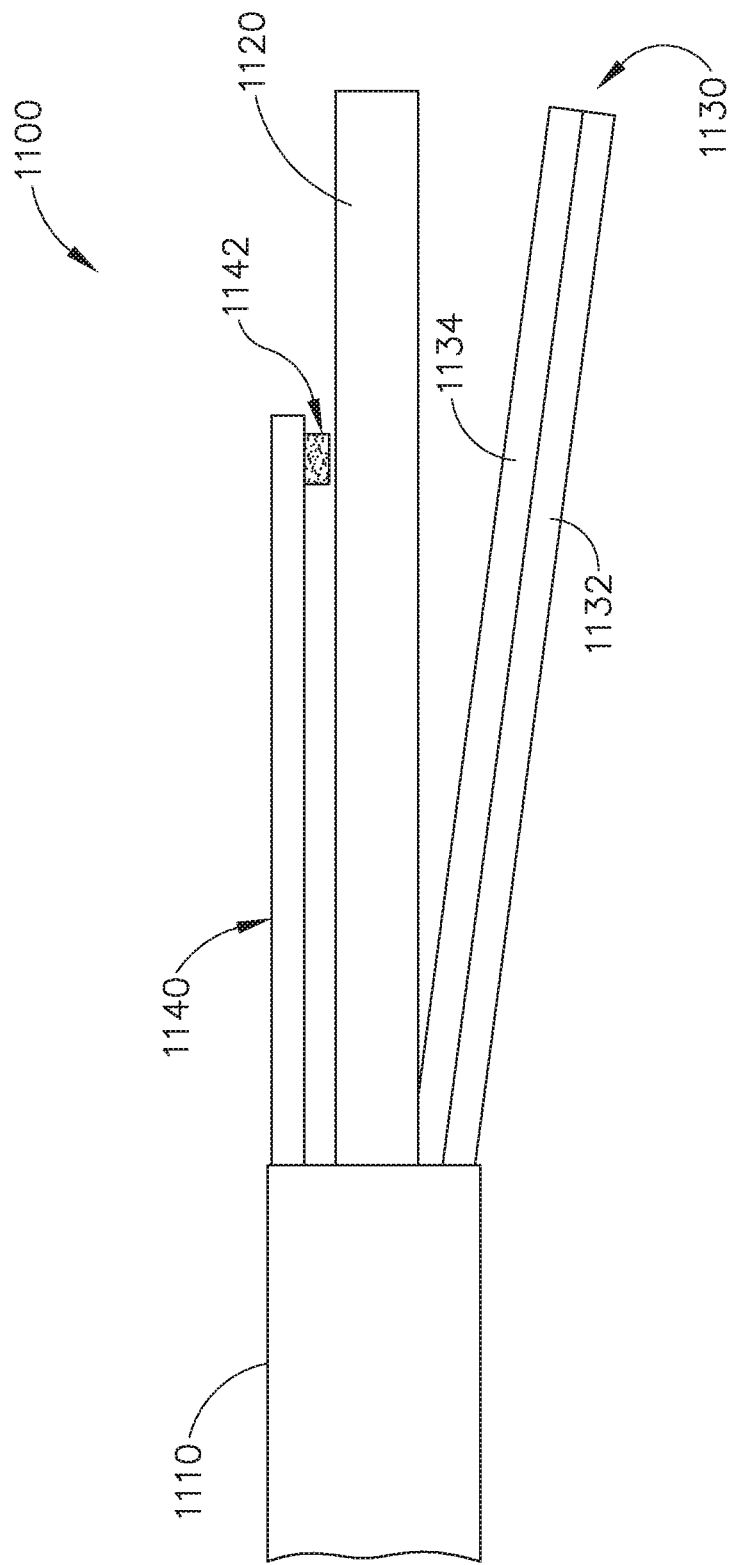
FIG. 27 depicts a partial side elevational view of another exemplary alternative end effector suitable for incorporation in the instrument of FIG. 1, with a clamp arm in an open position and with an ultrasonic blade in a home position in relation to a tube extension pad.

Outer tube (1110) includes a distally projecting tongue (1140), which further includes a polyimide pad (1142), which is positioned to engage ultrasonic blade (1120) at a location corresponding to a node associated with resonant ultrasonic vibrations communicated through ultrasonic blade (1120). Of course, polyimide is just one merely illustrative example of a material for pad (1142), and any other suitable material(s) may be used. As best seen in FIGS. 27 and 30, ultrasonic blade (1120) does not contact polyimide pad (1142) when ultrasonic blade (1120) is not under any kind of load. Thus, polyimide pad (1142) does not generate any additional heat in ultrasonic blade (1120) when ultrasonic blade is not under any kind of load.

Figure 28:
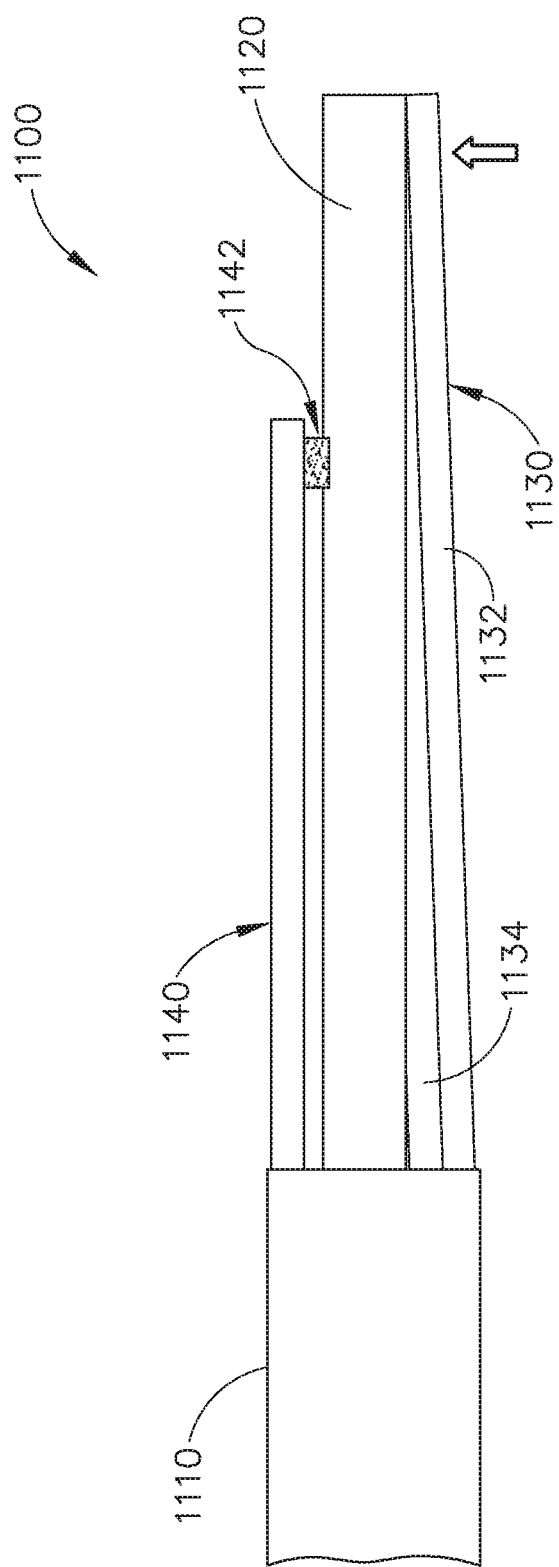
FIG. 28 depicts a partial side elevational view of the end effector of FIG. 27, with the clamp arm in a closed position and with the ultrasonic blade deflected into engagement with the tube extension pad.

As best seen in FIGS. 28 and 31, ultrasonic blade (1120) deflects into polyimide pad (1142) when clamp arm (1130) is pivoted into clamping engagement with ultrasonic blade (1120). When ultrasonic blade (1120) is activated while in contact with polyimide pad (1142), polyimide pad (1142) assists in generating additional heat in ultrasonic blade (1120) at the nodal region, thereby closing the nodal gap and addressing what might otherwise be an acoustic cold spot by providing a more even distribution of heat along ultrasonic blade (1120). Of course, while tissue is not shown in FIGS. 23 and 26, it should be understood that the same results may be obtained when tissue is clamped between clamp arm (1130) and ultrasonic blade (1120).

Figure 29:
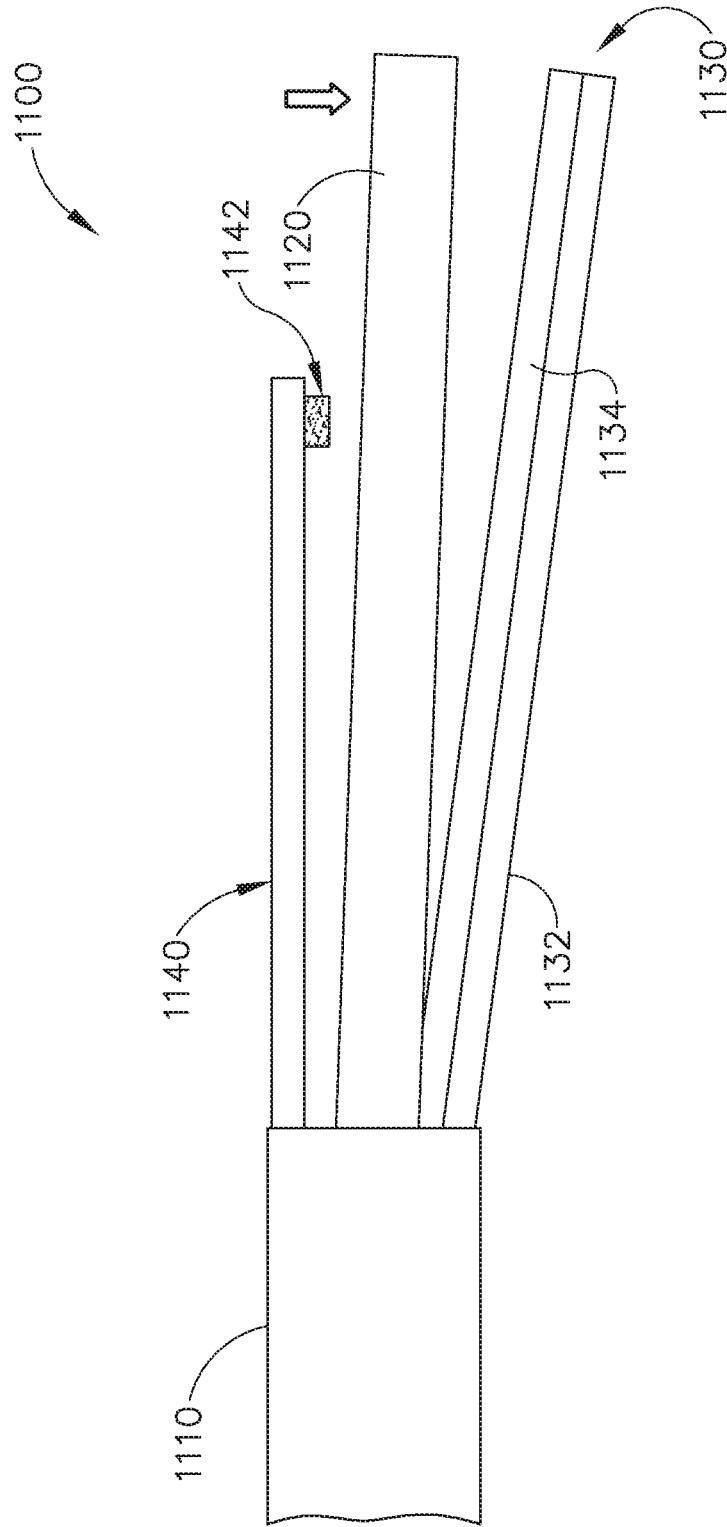
FIG. 29 depicts a partial side elevational view of the end effector of FIG. 27, with the clamp arm in an open position and with the ultrasonic blade deflected further away from the tube extension pad.

As best seen in FIGS. 29 and 32, ultrasonic blade (1120) deflects further away from polyimide pad (1142) when ultrasonic blade (1120) is used to perform a back-cutting operation (i.e., when the portion of ultrasonic blade (1120) opposite to clamp arm (1130) is pressed into tissue. Thus, polyimide pad (1142) does not provide any thermal impact during a back-cutting operation. This may be acceptable for users who only wish to use the distal-most portion of ultrasonic blade (1120) during back-cutting anyway, as the distal-most portion would already be sufficiently outside of a nodal gap since the distal tip is positioned at an anti-node.

VI. Miscellaneous

It should be understood that any of the versions of instruments described herein may include various other features in addition to or in lieu of those described above. By way of example only, any of the instruments described herein may also include one or more of the various features disclosed in any of the various references that are incorporated by reference herein. It should also be understood that the teachings herein may be readily applied to any of the instruments described in any of the other references cited herein, such that the teachings herein may be readily combined with the teachings of any of the references cited herein in numerous ways. Other types of instruments into which the teachings herein may be incorporated will be apparent to those of ordinary skill in the art.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of U.S. Pat. No. 6,783,524, entitled "Robotic Surgical Tool with Ultrasound Cauterizing and Cutting Instrument," published Aug. 31, 2004, the disclosure of which is incorporated by reference herein.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus for operating on tissue, the apparatus comprising:
(a) a shaft;
(b) an acoustic waveguide configured to transmit ultrasonic vibration, wherein the acoustic waveguide extends along the shaft; and (c) an end effector, wherein the end effector comprises:
  (i) an ultrasonic blade in acoustic communication with the acoustic waveguide, wherein the ultrasonic blade comprises a first location associated with a nodal point for transmitted ultrasonic vibrations, and
  (ii) a clamp arm pivotable relative to the ultrasonic blade between an open position and a closed position, wherein the clamp arm comprises a first portion and a second portion, wherein the second portion comprises a second location, wherein the second location of the second portion is configured to be adjacent to the first location of the ultrasonic blade when the clamp arm is in the closed position, wherein the first portion comprises a first coefficient of friction, wherein the second portion comprises a second coefficient of friction, wherein the second coefficient of friction is greater than the first coefficient of friction,
  wherein the clamp arm further comprises a third portion, wherein the second portion is located between the first portion and third portion.

2. The apparatus of claim 1, wherein the second portion is coupled with the first portion such that the second portion is raised from the first portion closer to the ultrasonic blade.

3. The apparatus of claim 1, wherein the first portion is proximal in relation to the second portion.

4. The apparatus of claim 3, wherein the third portion comprises a third coefficient of friction.

5. The apparatus of claim 4, wherein the third coefficient of friction is less than the second coefficient of friction.

6. The apparatus of claim 5, wherein the third coefficient of friction is equal to the first coefficient of friction.

7. The apparatus of claim 1, wherein the clamp arm further comprises a metallic arm, wherein the first portion is coupled with the metallic arm.

8. The apparatus of claim 7, wherein the second portion is also coupled with the metallic arm.

9. The apparatus of claim 1, wherein the first portion comprises a first melting temperature, wherein the second portion comprises a second melting temperature, wherein the second melting temperature is greater than the first melting temperature.

10. The apparatus of claim 1, wherein the first portion extends from a proximal position to a distal position, wherein the second portion is located between the proximal position and the distal position.

11. The apparatus of claim 1, wherein the first portion comprises a polytetrafluoroethylene pad.

12. The apparatus of claim 11, wherein the second portion comprises a polyimide pad.

13. The apparatus of 21, wherein the first portion has a different cross-sectional geometry as compared to the second portion.

14. An apparatus for operating on tissue, the apparatus comprising:
(a) a shaft;
(b) an acoustic waveguide configured to transmit ultrasonic vibration, wherein the acoustic waveguide extends along the shaft; and
(c) an end effector, wherein the end effector comprises:
  (i) an ultrasonic blade in acoustic communication with the acoustic waveguide, wherein the ultrasonic blade comprises a first location associated with a nodal point for transmitted ultrasonic vibrations, and
  (ii) a clamp arm pivotable relative to the ultrasonic blade between an open position and a closed position, wherein the clamp arm comprises a first portion and a second portion, wherein the second portion comprises a second location, wherein the second location of the second portion is configured to be adjacent to the first location of the ultrasonic blade when the clamp arm is in the closed position, wherein the first portion comprises a first melting temperature, wherein the second portion comprises a second melting temperature, wherein the second melting temperature is greater than the first melting temperature,
  wherein the clamp arm further comprises a third portion, wherein the third portion has a third melting temperature, and wherein the third melting temperature is different than each of the first and second melting temperatures of the first and second portions.

15. The apparatus of claim 14, wherein the third melting temperature is lower than the second melting temperature.

16. The apparatus of claim 15, wherein the second portion is located between the first portion and the third portion.

17. The apparatus of claim 14, wherein the first portion is longer than the second portion.

18. An apparatus for operating on tissue, the apparatus comprising:
(a) a shaft;
(b) an acoustic waveguide configured to transmit ultrasonic vibration, wherein the acoustic waveguide extends along the shaft; and
(c) an end effector, wherein the end effector comprises:
  (i) an ultrasonic blade in acoustic communication with the acoustic waveguide, wherein the ultrasonic blade comprises a first location associated with a nodal point for transmitted ultrasonic vibrations, and
  (ii) a clamp arm pivotable relative to the ultrasonic blade between an open position and a closed position, wherein the clamp arm comprises a first portion and a second portion, wherein the second portion comprises a second location, wherein the second location of the second portion is configured to be adjacent to the first location of the ultrasonic blade when the clamp arm is in the closed position, wherein the first portion comprises a first coefficient of friction, wherein the second portion comprises a second coefficient of friction, wherein the second coefficient of friction is greater than the first coefficient of friction,
  wherein the first portion extends from a proximal position to a distal position, wherein the second portion is located distal of the proximal position.

19. The apparatus of claim 18, wherein the second portion is located between the proximal position and the distal position.

20. The apparatus of claim 18, wherein the first portion includes a first pad, and wherein the second portion includes a second pad.

* * * * *